US010294496B2

(12) United States Patent
Conradie et al.

(10) Patent No.: US 10,294,496 B2
(45) Date of Patent: *May 21, 2019

(54) METHODS FOR BIOSYNTHESIZING 1,3 BUTADIENE

(71) Applicant: INVISTA North America S.á r.l., Wilmington, DE (US)

(72) Inventors: Alex Van Eck Conradie, Eaglescliffe (GB); Adriana Leonora Botes, East Cleveland (GB)

(73) Assignee: INVISTA NORTH AMERICA S.A.R.L., Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 14/334,190

(22) Filed: Jul. 17, 2014

(65) Prior Publication Data
US 2015/0079654 A1  Mar. 19, 2015

Related U.S. Application Data

(60) Provisional application No. 61/856,154, filed on Jul. 19, 2013.

(51) Int. Cl.
C12P 5/02 (2006.01)

(52) U.S. Cl.
CPC ....... *C12P 5/026* (2013.01); *C12Y 402/01127* (2013.01); *Y02E 50/343* (2013.01)

(58) Field of Classification Search
None
See application file for complete search history.

(56) References Cited

U.S. PATENT DOCUMENTS

| | | | |
|---|---|---|---|
| 8,703,455 B2 | 4/2014 | Marliere | |
| 8,741,612 B2 | 6/2014 | Campbell et al. | |
| 9,422,578 B2* | 8/2016 | Pearlman | C12P 5/02 |
| 9,422,580 B2* | 8/2016 | Pearlman | C12P 5/026 |
| 9,663,801 B2 | 5/2017 | Pearlman et al. | |
| 2011/0165644 A1 | 7/2011 | Marliere | |
| 2011/0300597 A1 | 12/2011 | Burk et al. | |
| 2012/0021478 A1 | 1/2012 | Osterhout et al. | |
| 2012/0122563 A1 | 5/2012 | Walker et al. | |
| 2012/0225466 A1 | 9/2012 | Burk et al. | |
| 2013/0189753 A1 | 7/2013 | Pearlman et al. | |
| 2013/0210104 A1 | 8/2013 | Pearlman et al. | |
| 2013/0309742 A1 | 11/2013 | Campbell et al. | |
| 2014/0065686 A1 | 3/2014 | Marliere | |
| 2014/0141482 A1 | 5/2014 | Pearlman et al. | |
| 2014/0186913 A1 | 7/2014 | Botes et al. | |
| 2015/0037860 A1 | 2/2015 | Botes et al. | |

FOREIGN PATENT DOCUMENTS

| | | |
|---|---|---|
| EP | 2336340 | 6/2011 |
| EP | 2336341 | 6/2011 |
| WO | WO 2009/155382 | 12/2009 |
| WO | WO 2010/001078 | 1/2010 |
| WO | WO 2010/099201 | 9/2010 |
| WO | WO 2011/011689 | 1/2011 |
| WO | WO 2011/076261 | 6/2011 |
| WO | WO 2011/076689 | 6/2011 |
| WO | WO 2011/076691 | 6/2011 |
| WO | WO 2011/079314 | 6/2011 |
| WO | WO 2011/140171 | 11/2011 |
| WO | WO 2012/018624 | 2/2012 |
| WO | WO 2012/052427 | 4/2012 |
| WO | WO 2012/174439 | 12/2012 |
| WO | WO 2013/007786 | 1/2013 |
| WO | WO 2013/020118 | 2/2013 |
| WO | WO 2013/028519 | 2/2013 |
| WO | WO 2013/036812 | 3/2013 |
| WO | WO 2013/040383 | 3/2013 |
| WO | WO 2013/057194 | 4/2013 |
| WO | WO 2013/082542 | 6/2013 |
| WO | WO 2013/090915 | 6/2013 |
| WO | WO 2013/092567 | 6/2013 |
| WO | WO 2013/150100 | 10/2013 |
| WO | WO 2013/173437 | 11/2013 |
| WO | WO 2013/181647 | 12/2013 |
| WO | WO 2013/188546 | 12/2013 |
| WO | WO 2013/192183 | 12/2013 |
| WO | WO 2014/001517 | 1/2014 |
| WO | WO 2014/033129 | 3/2014 |
| WO | WO 2014/064198 | 5/2014 |
| WO | WO 2014/085612 | 6/2014 |
| WO | WO 2014/015210 | 11/2014 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Kizer et al. Appl Environ Microbiol. May 2008;74(10):3229-41.*
Prather et al. Curr Opin Biotechnol. Oct. 2008;19(5):468-74.*
Singh et al. Curr Protein Pept Sci. 2017, 18, 1-11.*
Daniel et al., "Biochemistry of coenzyme B12-dependent glycerol and diol dehydratases and organization of the encoding genes," 1999, FEMS Microbiology Reviews, 22: 553-566.
Genbank accession No. E1XUJ2.1. Sep. 5, 2012, 2 pages.
International Preliminary Report on Patentability in International Application No. PCT/US2013/045430, dated Dec. 24, 2014, 12 pages.
Jin et al., "The selective addition of water to C=C bonds; enzymes are the best chemists," Chem Commun., 2011, 47:2502-2510 Kelada et al., "Delta-aminolevulinic acid dehydratase genotype and lead toxicity: A Huge Review," Am. J. Epidemiology, 2001, 154(1)1-13.
Kelada et al., "Delta-aminolevulinic acid dehydratase genotype and lead toxicity: A Huge Review," Am. J. Epidemiology, 2001, 154(1)1-13.

(Continued)

Primary Examiner — Christian L Fronda
(74) Attorney, Agent, or Firm — Licata & Tyrrell P.C.

(57) ABSTRACT

This document describes biochemical pathways for producing butadiene by forming two vinyl groups in a butadiene synthesis substrate. These pathways described herein rely on enzymes such as, inter alia, a decarboxylating thioesterase, cytochrome P450, or dehydratases for the final enzymatic step.

12 Claims, 7 Drawing Sheets

(56) References Cited

OTHER PUBLICATIONS

Luddeke et al. "Geraniol and Geranial Dehydrogenases Induced in Anaerobic Monoterpene Degradation by Castellaniella defragrans," Appl. and Environmental Microbiology, 2012, 78(7): 2128-2136.
Luddeke et al.," Enantiospecific (S)-(+)-linalool formation from beta-myrcene by linalool dehydratase-isomerase," Z Naturforsch C., Jul./Aug. 2011, 66(7-8):409-412.
Toraya, "Radical catalysis of B12 enzymes: structure, mechanism, inactivation and reactivation of diol and glycerol dehydratases," Cellular and Molecular Life Sciences, 2000, 57:106-127.
U.S. Final Office Action in U.S. Appl. No. 13/691,623, dated Dec. 9, 2014, 15 pages.
U.S. Final Office Action in U.S. Appl. No. 13/524,973, dated Dec. 22, 2014, 24 pages.
U.S. Non-Final Office Action in U.S. Appl. No. 13/092,115, dated Apr. 1, 2015, 21 pages.
Chinese Office Action in Chinese Application No. 201280040122.2, dated Jul. 17, 2015, 7 pages.
International Preliminary Report on Patentability and Written Opinion for PCT/US2013/072275, dated Jun. 2, 2015, 8 pages.
"Production of butadiene," China Synthetic Rubber Industry, Special issue of 1978, 21 pages (with partial English translation).
U.S. Non-Final Office Action in U.S. Appl. No. 13/916,156, dated Jul. 14, 2015, 35 pages.
U.S. Non-Final Office Action in U.S. Appl. No. 13/524,973, dated Jul. 23, 2015, 24 pages.
Zhang et al., "Genes encoding acyl-CoA dehydrogenase (AcdH) homologues from Streptomyces coelicolor and Streptomyces avermitilis provide insights into the metabolism of small branched-chain fatty acids and macrolide antibiotic production," Microbiology, 1999, 145(9):2323-2334, 12 pages.
Zhuang et al., "Divergence of function in the Hotdog-fold enzyme superfamily: the bacterial thioesterase YciA," Biochemistry, 2008, 47(9):2789-2796, 8 pages.
International Search Report and Written Opinion in Application No. PCT/U S2014/049786, dated Sep. 11, 2015, 17 pages.
Akatsuka et al., "The Serratia marcescens bioH gene encodes an esterase," Gene, Jan. 2003, 302:185-192.
Eriksen et al., "Protein Design for Pathway Engineering," Journal of Structural Biology, Apr. 2013, 185(2):234-242.
Invitation to pay additional fees and, where applicable, protest fee for PCT/US2015/036095, dated Sep. 18, 2015, 13 pages.
Lin et al., "The BioC O-Methyltransferase Catalyzed Methyl Esterification of Malonyl-Acyl Carrier Protein, an Essential Step in Biotin Synthesis," Journal of Biological Chemistry, Sep. 2012, 287(44):37010-37020.
Lin et al., "Biotin Sythesis Begins by Hijacking the Fatty Acid Synthetic Pathway," Nature Chem Biol., Sep. 2010, 6:682-688.
Uniprot Accession No. O32472, Jun. 11, 2014, 2 pages.
Uniprot Accession No. P0A6R0, May 14, 2014, 5 pages.
Uniprot Accession No. P0A8Z0, Jun. 11, 2014, 3 pages.
Uniprot Accession No. P0AGG2, Jun. 11, 2014, 3 pages.
Uniprot Accession No. P0AEK4, Jun. 11, 2014, 6 pages.
Uniprot Accession No. P0A6Q6, Jun. 11, 2014, 3 pages.
Uniprot Accession No. P0A953, Jun. 11, 2014, 4 pages.
Uniprot Accession No. P0AEK2, May 14, 2014, 4 pages.
Uniprot Accession No. P13001, Jun. 11, 2014, 4 pages.
Uniprot Accession No. Q5EU90, Feb. 19, 2014, 2 pages.
Uniprot Accession No. Q73Q47, May 14, 2014, 2 pages.
Uniprot Accession No. Q818X2, Jun. 11, 2014, 2 pages.
U.S. Final Office Action in U.S. Appl. No. 14/092,115, dated Oct. 27, 2015, 8 pages.
Westin et al., "The identification of a succinyl-CoA thioesterase suggests a novel pathway for succinate production in peroxisomes," J. Biol Chem, 2005, 280:38125-38132.
Barta et al., "Structural basis for nucleotide binding and reaction catalysis in mevalonate diphosphate decarboxylase," Biochemistry, 51(28):5611-5621, Epub Jul. 6, 2012.

Becker et al., "Metabolic flux engineering of L-lysine production in Corynebacterium glutamicum—over expression and modification of G6P dehydrogenase," *Journal of Biotechnology*, 132(2):99-109, Epub Jun. 6, 2007.
Brigham et al., "Engineering Ralstonia eutropha for Production of Isobutanol from CO2, H2, and O2," Advanced Biofuels and Bioproducts, Chapter 39, 1065-1090, 2012.
Brodkorb et al., "Linalool dehydratase-isomerase, a bifunctional enzyme in the anaerobic degradation of monoterpenes," *J Biol Chem.*, 285(40):30436-30442, Epub Jul. 27, 2010.
Buckel et al., "Glutaconate CoA-transferase from Acidaminococcus fermentans," *Eur J Biochem.*, 118(2):315-321, Aug. 1981.
Buckel et al., "2-Hydroxyacyl-CoA dehydratases, a novel family of molybdenum enzymes," J Inorganic Biochemistry, 2003, 96(1):53, 1 page.
Bugg et al., "The emerging role for bacteria in lignin degradation and bio-product formation," *Curr Opin Biotechnol.*, 22(3):394-400, Epub Nov. 9, 2010.
Chayabutra and Ju, "Degradation of n-hexadecane and its metabolites by Pseudomonas aeruginosa under microaerobic and anaerobic denitrifying conditions," *Appl Environ Microbiol.*, 66(2):493-498, Feb. 2000.
Chung and Rhee, "Overexpression of the (R)-specific enoyl-CoA hydratase gene from Pseudomonas chlororaphis HS21 in Pseudomonas strains for the biosynthesis of polyhydroxyalkanoates of altered monomer composition," Biosci. Biotechnol. Biochem., 76(3): 613-616, 2012.
Dhe-Paganon et al., "Mechanism of mevalonate pyrophosphate decarboxylase: evidence for a carbocationic transition state," *Biochemistry*, 33(45):13355-13362, Nov. 15, 1994.
Eikmanns and Buckel, "Crystalline green 5-hydroxyvaleryl-CoA dehydratase from Clostridium aminovalericum," *Eur. J. Biochem.*, 197(3):661-668, May 8, 1991.
European Communication Pursuant to Rules 161(1) and 162 EPC in application No. EP 12799032.3, dated Jun. 25, 2014, 13 pages.
Ferrandez et al., "Genetic characterization and expression in heterologous hosts of the 3-(3-hydroxyphenyl)propionate catabolic pathway of *Escherichia coli* K-12," *J. Bacteriol.*, 179(8): 2573-2581, Apr. 1997.
Forster-Fromme et al., "Biochemical characterization of isovaleryl-CoA dehydrogenase (LiuA) of Pseudomonas aeruginosa and the importance of liu genes for a functional catabolic pathway of methyl-branched compounds," FEMS Microbiol Lett, 2008, 286(1):78-84.
Fukui et al., "Expression and characterization of ®-specific enoyl coenzyme A hydratase involved in polyhydroxyalkanoate biosynthesis by Aeromonas caviae," J. Bacteriology, Feb. 1998, 180(3):667-673.
Gehret et al., "Terminal alkene formation by the thioesterase of curacin A biosynthesis: structure of a decarboxylating thioesterase," J. of Biological Chem., 2011, 186(16):14445-14454.
Genbank accession No. AAD44196.1, Oct. 15, 1999, 1 page.
Genbank accession No. AAG05403.1, Jan. 31, 2014, 2 pages.
Genbank accession No. AAV40818.1, Feb. 4, 2005, 1 page.
Genbank accession No. AAV40819.1, Feb. 4, 2005, 1 page.
Genbank accession No. AAV40820.1, Feb. 4, 2005, 1 page.
Genbank accession No. BAA21816.1, Aug. 19, 1997, 2 pages.
Genbank accession No. BAA92740, Aug. 1, 2007, 2 pages.
Genbank accession No. CAA32465.1, Jul. 26, 1995, 1 page.
Genbank accession No. CAA32466.1, Jul. 26, 1995, 1 page.
Genbank accession No. CAA42196.1, Oct. 16, 1995, 1 page.
Genbank accession No. CAA99573.1, Nov. 14, 2006, 2 pages.
Genbank accession No. NP_746661, Jun. 27, 2013, 2 pages.
Gogerty and Bobik, "Formation of isobutene from 3-hydroxy-3-methylbutyrate by diphosphomevalonate decarboxylase," *Appl Environ Microbiol.*, 76(24):8004-8010, Epub Oct. 22, 2010.
Gu et al., "Polyketide Decarboxylative chain Termination Preceded by 0-sulfonation in curacin A Biosynthesis," J. Am. Chemical Soc., Nov. 2009, 131(44):16033-16035.
Guan et al., "Cytochrome P450-dependent desaturation of lauric acid: isoform selectivity and mechanism of formation of 11-dodecenoic acid," *Chem Biol Interact.*, 110(1-2):103-121, Mar. 1998.

(56) References Cited

OTHER PUBLICATIONS

He and Spain, "A novel 2-aminomuconate deaminase in the nitrobenzene degradation pathway of Pseudomonas pseudoalcaligenes JS45," *J Bacteriol.*, 180(9):2502-2506, May 1998.
Hermann et al, "Industrial production of amino acids by coryneform bacteria," *J Biotechnol.*, 104(1-3):155-172, Sep. 2003.
International Preliminary Report on Patentability and Written Opinion for PCT/US2012/042757, dated Dec. 17, 2013, 7 pages.
International Preliminary Report on Patentability and Written Opinion for PCT/US2012/064407, dated May 13, 2014, 8 pages.
International Preliminary Report on Patentability and Written Opinion for PCT/US2012/067463, dated Jun. 3, 2014, 12 pages.
International Search Report and Written Opinion in Application No. PCT/US2013/072275, dated Mar. 6, 2014, 13 pages.
International Search Report and Written Opinion in Application No. PCT/US2013/045430, dated Feb. 3, 2014, 20 pages.
International Search Report and Written Opinion in Application No. PCT/US2014/048606, dated Oct. 31, 2014, 19 pages.
International Search Report and Written Opinion in Application No. PCT/US2014/049807, dated Nov. 5, 2014, 56 pages.
International Search Report in Application No. PCT/US2012/042757 dated Mar 6, 2013, 5 pages.
International Search Report in Application No. PCT/US2012/064407, dated Feb. 7, 2013, 13 pages.
International Search Report in Application No. PCT/US2012/067463, dated Jun. 17, 2013, 19 pages.
Invitation to pay additional fees and, where applicable, protest fee for PCT/US2012/067463, dated Mar 13, 2013, 17 pages.
Invitation to pay additional fees and, where applicable, protest fee for PCT/US2013/045430, dated Nov. 25, 2013, 6 pages.
Jang et al., "Bio-based production of C2-C6 platform chemicals," *Biotechnol Bioeng.*, 109(10):2437-2459, Epub Jul. 13, 2012.
Jaremko et al., "The initial metabolic conversion of levulinic acid in Cupriavidus necator," J Biotechnol, 2011, 155(3):293-298.
Kasai et al., "Uncovering the protocatechuate 2,3-cleavage pathway genes," *J Bacteriol.*, 191(21):6758-6768, Epub Aug. 28, 2009.
Kim et al., "An allylic ketyl radical intermediate in clostridial amino-acid fermentation," *Nature.*, 452(7184):239-242, Mar. 2008.
Kim et al., "Dehydration of ®-2-hydro9xyacyl-CoA to enoyl-CoA in the fermentation of α-amino acids by anaerobic bacteria," *FEMS Microbiol Rev*, 2004, 28(4):455-468, 14 pages.
Kim, "On the enzymatic mechanism of 2-hydroxyisocaproyl-CoA dehydratase from Clostridium difficile," 2004, Ph.D. dissertation, Philipps-Universität, Marburg, 2004.
Kizer et al., "Application of Functional Genomics to Pathway Optimization for Increased Isoprenoid Production," *Applied and Environmental Microbiology*, 2008, 74(10):3229-3241.
Köpke et al., "2,3-Butanediol production by acetogenic bacteria, an alternative route to chemical synthesis, using industrial waste gas," App Enviro Microbiol, 2011, 77(15):5467-5475.
Kuzma et al., "Bacteria produce the volatile hydrocarbon isoprene," *Curr Microbiol.*, 30(2):97-103, Feb. 1995.
Kuzuyama, "Mevalonate and nonmevalonate pathways for the biosynthesis of isoprene units," *Biosci Biotechnol Biochem.*, 66(8):1619-1627, Aug. 2002.
Lan et al., "ATP drives direct photosynthetic production of 1-butanol in cyanobacterial," PNAS, 2012, 109(16):6018-6023, 6 pages.
Lee et al., "Conversion of beta-methylbutyric acid to beta-hydroxy-beta-methylbutyric acid by Galactomyces reessii," Appl Environ Microbiol, 1997, 63(11):4191-4195, 5 pages.
Lee et al., "Synthesis of pure meso-2,3-butanediol from crude glycerol using an engineered metabolic pathway in *Escherichia coli*," Appl Biochem Biotechnol, 2012, 166(7):1801-1813.
Li et al., "Cupriavidus necator JMP134 rapidly reduces furfural with a Zn-dependent alcohol dehydrogenase," Biodegradation, 22(6):1215-1225, Nov. 2011.
Li et al., "JMP134 rapidly reduces furfural with a Zn-dependent alcohol dehydrogenase," Biodegradation, 2011, 22(6):1215-1225, 11 pages.

Lim et al., "Amplification of the NADPH-Related Genes zwf and gnd for the Oddball Biosynthesis of PHBin an *E. coli* Tranformant Harboring a Cloned phbCAB Operon," J Bioscience and Bioengineering, 2002, 93(6):543-549.
Liu et al., "Microbial production of R-3-hydroxybutyric acid by recombinant *E. coli* harboring genes of phbA, phbB, and tesB," *Appl Microbiol Biotechnol.*, 76(4):811-818, Epub Jul. 4, 2007.
Luo et al., "Production of 3-hydroxypropionic acid through propionaldehyde dehydrogenase PduP mediated biosynthetic pathway in Klebsiella pneumoniae," *Bioresour Technol.*, 103(1):1-6, Epub Oct. 2, 2011.
Martin et al., "Engineering a Mevalonate pathway to *Escherichia coli* for production of terpenoids," *Nature Biotechnology*, 2003, 21:796-802.
Martin et al., "High-titer production of monomeric hydroxyl valerates from levulinic acid I Pseudomonas putida," J Biotechnol, 2009, 139(1):61-67.
McCarthy et al., "Structural basis of functional group activation by sulfotransferases in complex metabolic pathways," ACS Chem. Biol., 2012, 7:1994-2003.
Meijnen et al., "Improved p-hydroxybenzoate production by engineered Pseudomonas putida S12 by using a mixed-substrate feeding strategy," Appl Microbiol Biotechnol, 2011, 90(3):885-893.
Mo et al., "Biosynthesis of the allylmalonyl-CoA extender unit for the FK506 polyketide synthase proceeds through a dedicated polyketide synthase and facilitates the mutasynthesis of analogues," *J Am Chem Soc.*, 133(4):976-985, Epub Dec. 22, 2010 [author manuscript].
Morone et al., "Increasing diterpene yield with a modular metabolic engineering system in *E. coli*: comparison of MEV and MEP isoprenoid precursor pathway engineering," *Applied Microbiology and Biotechnology*, 2010, 85:1893-1906.
Muraki et al., "Prokaryotic homologs of the eukaryotic 3-hydroxyanthranilate 3,4-dioxygenase and 2-amino-3-carboxymuconate-6-semialdehyde decarboxylase in the 2-nitrobenzoate degradation pathway of Pseudomonas fluorescents strain KU-7," *Appl Environ Microbiol.*, 69(3):1564-1572, Mar. 2003.
Ohashi et al., "Continuous production of lactic acid from molasses by perfusion culture of Lactococcus lactis using a stirred ceramic membrane reactor," J Bioscience and Bioengineering, 1999, 87(5):647-654.
Papanikolaou et al., "Citric acid production by Yarrowia lipolytica cultivated on olive-mill wastewater-based media," Bioresour. Technol., 2008, 99(7):2419-2428.
Pérez-Pantoja et al., "Metabolic reconstruction of aromatic compounds degradation from the genome of the amazing pollutant-degrading bacterium Cupriavidus necator JMP134," FEMS Microbiol Rev., 2008, 32(5):736-794.
Prather et al., "De nova biosynthetic pathways: rational design of microbial chemical factories," 2008, 19:468-474.
Prybylski et al., "Third-generation feed stocks for the clean and sustainable biotechnological production of bulk chemicals: synthesis of 2-hydroxyisobutyric acid," Energy, Sustainability and Society, 2012, 2:11.
Ramsay et al., "Use of a Nylon Manufacturing Waste as an Industrial Fermentation Substrate," Appl Environ Microbiol, 1986, 52(1):152-156.
Rettie et al., "CYP4 Isozyme Specificity and the Relationship between co-Hydroxylation and Terminal Desaturation of Valproic Acid," Biochemistry, 34(24): 7889-7895 (1995).
Rude et al., "Terminal olefin (1-alkene) biosynthesis by a novel p450 fatty acid decarboxylase from Jeotgalicoccus species," Appl. Environ. Microbiol., 2011, 77(5):1718-1727.
Schäfer et al., "Synthesis of short-chain diols and unsaturated alcohols from secondary alcohol substrates by the Rieske nonheme mononuclear iron oxygenase MdpJ.," Appl Environ Microbiol., 78(17):6280-6284, Epub Jun. 29, 2012.
Scherf and Buckel, "Purification and properties of an iron-sulfur and FAD-containing 4-hydroxybutyryl-CoA dehydratase/vinylacetyl-CoA delta 3-delta 2-isomerase from Clostridium aminobutyricum," *Eur J Biochem.*, 215(2):421-429, Jul. 15, 1993.

(56) References Cited

OTHER PUBLICATIONS

Scherf et al., "Succinate-ethanol fermentation in Clostridium kluyveri: purification and characterization of 4-hydroxybutyryl-CoA dehydratase/vinylacetyl-CoA delta 3-delta 2-isomerase," *Arch Microbiol.*, 161(3):239-245, 1994.

Seedorf et al., "The genome of Clostridium kluyveri, a strict anaerobe with unique metabolic features," Proc Natl Acad Sci USA, 2008, 105(6):2128-2133.

Shen et al., "Driving Forces Enable High-Titer Anaerobic 1-Butanol Synthesis in *Escherichia coli*," Appl Environ Microbiol., 2011, 77(9):2905-2915.

Silver and Fall, "Characterization of aspen isoprene synthase, an enzyme responsible for leaf isoprene emission to the atmosphere," *J Biol Chem.*, 270(22):13010-13016, Jun. 2, 1995.

Sweeney et al., "Physiologically based pharmacokinetic modeling of 1,3-butadiene, 1,2-epoxy-3-butene, and 1,2:3,4-diepoxybutane toxicokinetics in mice and rats," *Carcinogenesis.*, 18(4):611-625, Apr. 1997.

Tseng et al., "Biosynthesis of chiral 3-hydroxyvalerate from single propionate-unrelated carbon sources in metabolically engineered *E. coli*," *Microb Cell Fact.*, 9:96, Nov. 27, 2010.

Tsuge et al., "Molecular characterization and properties of (R)-specific enoyl-CoA hydratases from Pseudomonas aeruginosa: metabolic tools for synthesis of polyhydroxyalkanoates via fatty acid beta-oxidation," *Int J Biol Macromol.*, 31(4-5):195-205, Jan. 2003.

Ulmer et al., "Bacterial production of poly(.beta.-hydroxyalkanoates) containing unsaturated repeating units by Rhodospirillum rubrum," Macromolecules, 27(7):1675-1679, 1994.

Uniprot Accession No. B8ZLF3, Jun. 15, 2010, 2 pages.
Uniprot Accession No. I3RA72, Sep. 5, 2012, 2 pages.
Uniprot Accession No. P32377, Jun. 15, 2010, 4 pages.
Uniprot Accession No. Q7CCL9, Jun. 15, 2010, 2 pages.

Upton and Mckinney, "Role of the methylcitrate cycle in propionate metabolism and detoxification in *Mycobacterium smegmatis*," *Microbiology*, 153(Pt 12):3973-3982, Dec. 2007.

U.S. Non-Final Office Action in U.S. Appl. No. 13/524,973, dated Jun. 11, 2014, 17 pages.

U.S. Non-Final Office Action in U.S. Appl. No. 13/691,623, dated Jun. 25, 2014, 13 pages.

Van Leeuwen et al., "Fermentative production of isobutene," Appl Microbiol Biotechnol, 2012, 93(4):1377-1387.

Wang and Liao, "Alteration of product specificity of Rhodobacter sphaeroides phytoene desaturase by directed evolution," *J Biol Chem.*, 276(44):41161-41164, Epub Aug. 28, 2001.

Wee et al., "Biotechnological production of lactic acid and its recent applications," Food Technol. Biotechnol., 2006, 44(2):163-172.

Wendt et al., "Crystal structure of the carboxyltransferase subunit of the bacterial sodium ion pump glutaconyl-coenzyme A decarboxylase," *EMBO J.*, 22(14):3493-3502, Jul. 15, 2003.

White, "Butadiene production process overview," *Chem Biol Interact.*, 166(1-3):10-14, Epub Jan. 26, 2007.

Yang et al., "Enhancing production of bio-isoprene using hybrid MVA pathway and isoprene synthase in *E. coli*," *PLoS One*, Apr. 2012, 7:1-7.

Yang et al., "Value-added uses for crude glycerol-a byproduct of biodiesel production," Biotechnology for Biofuels, 2012, 5:13, 10 pages.

Zhao et al., "Biosynthesis of isoprene in *Escherichia coli* via methylerythritol phosphate (MEP) pathway," *Applied Microbiology and Biotechnology*, Apr. 2011, 90:1915-1922.

International Preliminary Report on Patentability in PCT/US2014/048606 dated Feb. 11, 2016.

Office communication dated Apr. 23, 2015 from U.S. Appl. No. 13/691,623, filed Nov. 30, 2012.

Office communication dated Jul. 17, 2015 from U.S. Appl. No. 13/691,623, filed Nov. 30, 2012.

Office communication dated Dec. 3, 2015 from U.S. Appl. No. 13/916,156, filed Jun. 12, 2013.

Office communication dated Dec. 7, 2015 from U.S. Appl. No. 13/691,623, filed Nov. 30, 2012.

Office communication dated Apr. 7, 2016 from U.S. Appl. No. 13/916,156, filed Jun. 12, 2013.

Office communication dated Apr. 20, 2016 from U.S. Appl. No. 13/524,973, filed Jun. 15, 2012.

Office communication dated Apr. 20, 2016 from U.S. Appl. No. 13/916,156, filed Jun. 12, 2013.

Office communication dated May 4, 2016 from U.S. Appl. No. 13/691,623, filed Nov. 30, 2012.

Office communication dated May 17, 2016 from U.S. Appl. No. 13/916,156, filed Jun. 12, 2013.

Office communication dated Jun. 16, 2016 from EP 12 799 032.3-1501 filed Nov. 30, 2012.

Office communication dated Aug. 12, 2016 from EP 13 739 305.4-1501 filed Jun. 12, 2013.

Office communication dated Aug. 23, 2016 from CN 201280068870.1 filed Nov. 30, 2012.

Office communication dated Aug. 30, 2016 from U.S. Appl. No. 13/524,973, filed Jun. 15, 2012.

Office communication dated Nov. 8, 2016 from CN 201380043586.3 filed Jun. 12, 2013.

Office communication dated Jan. 26, 2017 from U.S. Appl. No. 13/524,973, filed Jun. 15, 2012.

Office communication dated Jun. 2, 2017 from CN 201280068870.1 filed Nov. 30, 2012.

Office communication dated Jul. 10, 2017 from EP 12 799 032.3-1501 filed Nov. 30, 2012.

Office communication dated Jul. 12, 2017 from CN 201380043586.3 filed Jun. 12, 2013.

Office communication dated Oct. 25, 2017 from EP 13 739 305.4-1501 filed Jun. 12, 2013.

Office communication dated Jan. 4, 2018 from CN 201280068870.1 filed Nov. 30, 2012.

Office communication dated Mar. 23, 2018 from CN 201380043586.3 filed Jun. 12, 2013.

Office communication dated Aug. 2, 2018 from CN 201280068870.1 filed Nov. 30, 2012.

International Preliminary Report on Patentability in PCT/US2014/049789 dated Aug. 5, 2014.

* cited by examiner

METHODS FOR BIOSYNTHESIZING 1,3 BUTADIENE

CROSS-REFERENCE TO RELATED APPLICATIONS

This application claims priority of U.S. Provisional Application Ser. No. 61/856,154, filed Jul. 19, 2013. The contents of the prior application is incorporated herein by reference in its entirety.

TECHNICAL FIELD

This invention relates to methods for biosynthesizing 1,3-butadiene, and more particularly to synthesizing 1,3-butadiene using one or more isolated enzymes such as dehydrogenases, dehydratases, decarboxylating thioesterases, decarboxylating cytochrome P450s or using recombinant host cells expressing one or more of such enzymes.

BACKGROUND 1,3-Butadiene (sometimes referred to herein as "butadiene") is an important monomer for the production of synthetic rubbers including styrene-butadiene-rubber (SBR), polybutadiene (PB), styrene-butadiene latex (SBL), acrylonitrile-butadiene-styrene resins (ABS), nitrile rubber, and adiponitrile. Adiponitrile is used in the manufacture of Nylon-66 (White, Chemico-Biological Interactions, 2007, 166, 10-14).

Butadiene is typically produced as a co-product from the steam cracking process, distilled to a crude butadiene stream, and purified via extractive distillation (White, Chemico-Biological Interactions, 2007, 166, 10-14).

On-purpose butadiene has been prepared among other methods by dehydrogenation of n-butane and n-butene (Houdry process); and oxidative dehydrogenation of n-butene (Oxo-D or O-X-D process) (White, Chemico-Biological Interactions, 2007, 166, 10-14).

Industrially, 95% of global butadiene production is undertaken via the steam cracking process using petrochemical-based feedstocks such as naphtha. Production of on-purpose butadiene is not significant, given the high cost of production and low process yield (White, Chemico-Biological Interactions, 2007, 166, 10-14).

Given reliance on petrochemical feedstocks and, for on-purpose butadiene, energy intensive catalytic steps; biotechnology offers an alternative approach via biocatalysis. Biocatalysis is the use of biological catalysts, such as enzymes, to perform biochemical transformations of organic compounds.

Accordingly, against this background, it is clear that there is a need for sustainable methods for producing intermediates, in particular butadiene, wherein the methods are biocatalyst based (Jang et al., Biotechnology & Bioengineering, 2012, 109(10), 2437-2459).

Both bioderived feedstocks and petrochemical feedstocks are viable starting materials for the biocatalysis processes.

The generation of two vinyl groups into medium carbon chain length enzyme substrates is a key consideration in synthesizing butadiene via biocatalysis processes.

There are no known enzyme pathways leading to the synthesis of butadiene in prokaryotes or eukaryotes. Three potential pathways have been suggested for producing 1,3-butadiene from biomass-sugar: (1) from acetyl-CoA via crotonyl-CoA; (2) from erythrose-4-phosphate; and (3) via a condensation reaction with malonyl-CoA and acetyl-CoA. However, no information using these strategies has been reported (Jang et al., Biotechnology & Bioengineering, 2012, 109(10), 2437-2459).

SUMMARY

This document is based at least in part on the discovery that it is possible to construct biochemical pathways for producing medium length (e.g., C5) chain carbon metabolites, in which two vinyl groups can be formed, leading to the synthesis of butadiene. These pathways, which are described herein, rely on enzymes such as sulphotransferases and decarboxylating thioesterases, decarboxylating cytochrome P450s and dehydratases for the final enzymatic step.

It was not previously known that enzymes capable of forming two terminal vinyl groups in a medium chain carbon metabolite existed or could be produced for the synthesis of butadiene.

Thus, in one aspect, this document provides enzymes that can convert butadiene synthesis substrates into butadiene. As used herein, the term "butadiene synthesis substrate" refers to a substrate for which an enzyme can catalyze a reaction that results directly in 1,3-butadiene or in a product that, after one or more enzyme-catalyzed reactions, is converted to 1,3-butadiene. Relevant enzymes are those disclosed herein as having this activity.

In some embodiments, the first vinyl group leading to the synthesis of butadiene is enzymatically formed in pent-2-enoyl-[acp] to produce 2,4-pentadienoyl-[acp]. (FIG. 2).

In some embodiments, the first vinyl group leading to the synthesis of butadiene is enzymatically formed in lactoyl-CoA, 3-hydroxypropionyl-CoA, or propanoyl-CoA to produce propenyl-CoA. (FIG. 3).

In some embodiments, the first vinyl group leading to the synthesis of butadiene is enzymatically formed in 5-hydroxypentanoyl-CoA (via 5-hydroxy-pent-2-enoyl-CoA as intermediate) to produce 2,4-pentadienoyl-CoA. (FIG. 4).

In some embodiments, the first vinyl group leading to the synthesis of butadiene is enzymatically formed in 4-hydroxy-pent-2-enoyl-CoA to produce pent-2,4-dienoyl CoA (2,4-pentadienoyl-CoA). (FIG. 6).

In some embodiments, the first vinyl group leading to the synthesis of butadiene is enzymatically formed in 2-butanol (butan-2-ol), 2-buten-1-ol or 2-buten-1-ol diphosphate to produce 3-buten-2-ol. (FIG. 5).

In some embodiments, the second vinyl group leading to the synthesis of butadiene is formed in (R) 3-hydroxypent-4-enoyl-[acp] or (R) 3-hydroxypent-4-enoyl-CoA by sulphotransferase followed by decarboxylating thioesterase activity ((i) and (vi) in FIG. 7).

In some embodiments, the second vinyl group leading to the synthesis of butadiene is formed in (R) 3-hydroxypent-4-enoyl-[acp] or (R) 3-hydroxypent-4-enoyl-CoA by phosphotransferase followed by thioesterase activity ((ii) and (iii) in FIG. 7).

In some embodiments, the second vinyl group leading to the synthesis of butadiene is formed in pent-4-enoyl-CoA by thioesterase activity followed by activity of a decarboxylating cytochrome P450 in the CYP152 family ((v) in FIG. 7).

In some embodiments, the second vinyl group leading to the synthesis of butadiene is formed in 3-buten-2-ol by linalool dehydratase classified in EC 4.2.1.127 or a dehydratase classified under EC 4.2.1.—(such as one isolated from species such as *Aquincola tertiaricarbonis* or *Methylibium petroleiphilum* PM1) ((vi) in FIG. 7).

In one aspect, this document features a method for the biosynthesis of butadiene. The method includes forming two terminal vinyl groups in a butadiene synthesis substrate. A first vinyl group can be enzymatically formed in the butadiene synthesis substrate to produce a compound selected from the group consisting of 2,4-pentadienoyl-[acp], propenoyl-CoA, 2,4-pentadienoyl-CoA, 3-buten-2-ol and pent-4-enoyl-CoA In one aspect, 2,4-pentadienoyl-[acp] can be produced by forming a first vinyl group in pent-2-enoyl-[acp] using an acyl-[acp] dehydrogenase such as encoded by tcsD (FIG. 2). The pent-2-enoyl-[acp] can be produced by converting (R)-3-hydroxypentanoyl-[acp] using a 3-hydroxyacyl-[acp] dehydratase classified under EC 4.2.1.59 such as encoded by fabZ (FIG. 2). The (R)-3-hydroxypentanoyl-[acp] can be produced by converting (R)-3-oxopentanoyl-[acp] using a 3-oxoacyl-[acp] reductase classified in EC 1.1.1.100 such as encoded by fabG or AnlG (FIG. 2). The (R)-3-oxopentanoyl-[acp] can be produced by converting propanoyl-CoA using a β-ketoacyl-[acp] synthase such as encoded by tcsA and tcsB (FIG. 2). The propanoyl-CoA can be produced via a number of pathways (FIG. 1).

In one aspect, propenoyl-CoA can be produced by forming a first vinyl group in (i) 3-hydroxypropionyl-CoA using a 3-hydroxypropionyl-CoA dehydratase classified in EC 4.2.1.116, (ii) propanoyl-CoA using a acyl-CoA dehydrogenase classified in EC 1.3.8.-(1,7) or a 2-methylacyl-CoA dehydrogenase classified in EC 1.3.99.12 or (iii) lactoyl-CoA using a lactoyl-CoA dehydratase classified in EC 4.2.1.54 (FIG. 3).

The propanoyl-CoA can be produced via a number of pathways (FIG. 1).

The 3-hydroxypropionyl-CoA can be produced by converting 3-hydroxypropionate using 3-hydroxyisobutyryl-CoA hydrolase classified in EC 6.2.1.—(FIG. 3). The 3-hydroxypropionate can be produced by converting malonate semialdehyde using 3-hydroxyproprionate dehydrogenase classified in EC 1.1.1.59 (FIG. 3). The malonate semialdehyde can be produced by converting malonyl-CoA using malonyl-CoA reductase classified in EC 1.2.1.75 (FIG. 3).

The lactoyl-CoA can be produced by converting L-lactate using propionate-CoA transferase classified in EC 2.8.3.1 (FIG. 3). The L-lactate can be produced by converting pyruvate using L-lactate dehydrogenase classified in EC 1.1.1.27 (FIG. 3).

In one aspect, the 2,4-pentadienoyl-CoA can be produced by forming a first vinyl group in 5-hydroxypentanoyl-CoA using a 5-hydroxypentanoyl-CoA dehydratase classified in EC 4.2.1.—(FIG. 4) (such as one isolated from *Clostridium viride*). The 5-hydroxypentanoyl-CoA can be produced by converting 5-hydroxypentanoate using 5-hydroxypentanoyl-CoA CoA-transferase classified in EC 2.8.3.14 (FIG. 4). The 5-hydroxypentanoate can be produced by converting 5-oxopentanoic acid using a 5-hydroxypentanoate dehydrogenase (FIG. 4) (such as one encoded by cpnD). The 5-oxopentanoic acid can be produced by converting 5-aminovalerate (5-aminovaleric acid) using 5-aminovalerate transaminase classified in EC 2.6.1.48 (FIG. 4). The 5-aminovalerate can be produced via a number of pathways (FIG. 4).

In one aspect, 2,4-pentadienoyl-CoA (pent-2,4-dienoyl-CoA) can be produced by forming a first vinyl group in 4-hydroxypent-2-enoyl-CoA using a dehydratase such as linalool dehydratase classified under EC 4.2.1.127 or a dehydratase classified under EC 4.2.1.—(such as one isolated from species such as *Aquincola tertiaricarbonis* or *Methylibium petroleiphilum* PM1) (FIG. 6). The 4-hydroxypent-2-enoyl-CoA can be produced by converting 4-hydroxypentanoyl-CoA using a reversible trans-2-enoyl-CoA reductase such as one classified under EC 1.3.1.—(e.g., EC 1.31.8 or EC 1.3.1.38) or EC 1.3.1.44 (e.g., one encoded by ter or tdter) (FIG. 6). The 4-hydroxypentanoyl-CoA can be produced by converting levulinyl-CoA using a secondary alcohol dehydrogenase classified under EC 1.1.1.B4 or a 3-hydroxybutanoate oxidoreductase homologue classified under EC 1.1.1.30. (FIG. 6). The levulinyl-CoA can be produced by converting levulinic acid using a CoA-ligase classified in EC 6.2.1.-. (FIG. 6).

In one aspect, the pent-4-enoyl-CoA can be produced by forming a first vinyl group into 4-hydroxypentanoyl-CoA using a dehydratase such as linalool dehydratase classified in EC 4.2.1.127 or a dehydratase classified under EC 4.2.1.—(such as one isolated from species such as *Aquincola tertiaricarbonis* or *Methylibium petroleiphilum* PM1) (FIG. 6). The 4-hydroxypentanoyl-CoA can be produced by converting levulinyl-CoA using a secondary alcohol dehydrogenase classified under EC 1.1.1.B4 or a 3-hydroxybutanoate oxidoreductase homologue classified under EC 1.1.1.30. (FIG. 6). The levulinyl-CoA can be produced by converting levulinic acid using a CoA-ligase classified under EC 6.2.1.-. (FIG. 6).

In one aspect, the 3-buten-2-ol can be produced by forming a first vinyl group in (i) butan-2-ol using a desaturase or a monooxygenase such as encoded by MdpJ, (ii) 2-buten-1-ol using an isomerase (classified in EC5.4.4.-), (iii) 2-buten-1-ol diphosphate using a 2-methyl-3-buten-2-ol synthase (such as that encoded by Tps-MBO1) or (iv) 3-buten-2-one using a (R)-specific secondary alcohol dehydrogenase (classified in EC1.1.1.B4. (FIG. 5).

The butan-2-ol can be produced by converting butanone (butan-2-one) using a (R)-specific secondary alcohol dehydrogenase classified under EC 1.1.1.B4 (FIG. 5). The butan-2-one can be produced by converting 2,3-butanediol using a propanediol dehydratase classified under EC 4.2.1.28 or converting 3-oxopentanoate using an acetoacetate decarboxylase classified under EC 4.1.1.4 (FIG. 5). The 2,3 butanediol can be produced by converting (R)-acetoin using a (R,R)-butanediol dehydrogenase classified under EC 1.1.1.4. (R)-acetoin can be produced by converting 2-acetolactate using an acetolactate decarboxylase classified under EC 4.1.1.5 (FIG. 5) The 2-acetolactate can be produced by converting pyruvate using an acetolactate synthase classified under EC 2.2.1.6 (FIG. 5). The 3-oxopentanoate can be produced by converting 3-oxopentanoyl-CoA using a thioesterase classified under EC 3.1.2.-, such as the gene product of YciA, tesB, tesA or fadM (FIG. 5). The 3-oxopentanoyl-CoA can be produced by converting propanoyl-CoA using a β-ketothiolase classified under EC 2.3.1.16. The propanoyl-CoA can be produced via a number of pathways (FIG. 1).

The 2-buten-1-ol can be produced by converting 2-buten-1-al using an allyl-alcohol dehydrogenase classified under EC 1.1.1.54 (FIG. 5). The 2-buten-1-al can be produced by converting crotonic acid using a long-chain-aldehyde dehydrogenase classified under EC 1.2.1.48 (FIG. 5). Crotonic acid can be produced by converting crotonyl-CoA using a succinate-CoA ligase classified under EC 6.2.1.5 (FIG. 5).

The 2-buten-1-ol diphosphate can be produced by converting 2-buten-1-ol phosphate using a phosphomevalonate kinase (classified under EC 2.7.4.2) or by converting 2-buten-1-ol using a diphosphotransferases such as a thiaminediphosphokinase classified under (EC 2.7.6.2) (FIG. 5). The 2-buten-1-ol phosphate can be produced by converting 2-buten-1-ol using mevalonate kinase (classified under EC 2.7.1.36) (FIG. 5).

The 3-buten-2-one can be produced by converting 3-oxopent-4-enoate using an acetolactate decarboxylase classified under EC 4.1.1.4 (FIG. 5). The 3-oxopent-4-enoate can be produced by converting 3-oxopent-4-enoyl-CoA using a thioesterase classified under EC 3.1.2.—such as the gene product of YciA, tesB, tesA or fadM (FIG. 5). The 3-oxopent-4-enoyl-CoA can be produced by converting propenyl-CoA using a β-ketothiolase classified under EC 2.3.1. such as EC 2.3.1.16. (FIG. 5).

The second vinyl group can be enzymatically formed in 3-sulphoryl-pent-4-enoyl-[acp] by a decarboxylating thioesterase such as that encoded by CurM TE ((i) in FIG. 7)

The second vinyl group can be enzymatically formed in 3-phospho-pent-4-enoyl-[acp] by a decarboxylating thioesterase such as that encoded by CurM TE ((ii) in FIG. 7).

The second vinyl group can be enzymatically formed in 3-sulphoryl-pent-4-enoyl-CoA by a decarboxylating thioesterase ((iv) in FIG. 7).

The second vinyl group can be enzymatically formed in 3-phospho-pent-4-enoyl-CoA by a decarboxylating thioesterase ((iii) in FIG. 7)

The second vinyl group can be enzymatically formed in pent-4-enoate by decarboxylating cytochrome P450 in the CYP152 family ((v) in FIG. 7).

The second vinyl group can be enzymatically formed in 3-buten-2-ol by linalool dehydratase (classified under EC 4.2.1.127) or a dehydratase classified under EC 4.2.1.— (such as one isolated from species such as *Aquincola tertiaricarbonis* or *Methylibium petroleiphilum* PM1) ((vi) in FIG. 7).

In any of the methods described herein, the method can be performed using isolated enzymes, using cell lysates comprising the enzymes, or using a recombinant host.

The recombinant host can be anaerobically, micro-aerobically or aerobically cultivated.

Recombinant host cells can be retained in ceramic hollow fiber membranes to maintain a high cell density during fermentation.

The principal carbon source fed to the fermentation can derive from biological or non-biological feedstocks. For example, the biological feedstock is, or derives from, monosaccharides, disaccharides, lignocellulose, hemicellulose, cellulose, levulinic acid, furfural, lignin, triglycerides such as glycerol and fatty acids, agricultural waste or municipal waste. The non-biological feedstock is, or derives from, either natural gas, syngas, $CO_2/H_2$, methanol, ethanol, non-volatile residue (NVR) or caustic wash waste stream from cyclohexane oxidation processes.

The host microorganism can be a prokaryote from the genus *Escherichia* such as *Escherichia coli*; from the genus *Clostridia* such as *Clostridium ljungdahlii, Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*.

The host microorganism can be a eukaryote from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*.

In any of the recombinant hosts described herein, the enzymes catalyzing the hydrolysis of propionyl-CoA and acetyl-CoA can be attenuated; the enzymes consuming propanoyl-CoA via the methyl-citrate cycle can be attenuated; the enzymes consuming propanoyl-CoA to pyruvate can be attenuated; the enzymes consuming propanoyl-CoA to malonyl-CoA can be attenuated; a feedback-resistant threonine deaminase can be genetically engineered into the host organism; the β-ketothiolases catalyzing the condensation of acetyl-CoA to acetoacetyl-CoA such as the gene products of AtoB or phaA can be attenuated; the polymer synthase enzymes in a host strain that naturally accumulates polyhydroxyalkanoates can be attenuated; a gene encoding a phosphotransacetylase, such as pta, can be attenuated; a gene encoding an acetate kinase degrading propanoate, such as ack, can be attenuated; a gene encoding the degradation of pyruvate to lactate can be attenuated; a gene encoding the degradation of phophoenolpyruvate to succinate such as frdBC can be attenuated; a gene encoding the degradation of acetyl-CoA to ethanol such as adhE can be attenuated; the enzymes catalyzing anaplerotic reactions supplementing the citric acid cycle intermediates can be amplified; the 3'-phosphoadenosine 5'-phosphosulfate synthase (EC 2.7.7.4, EC 2.7.7.5) and 3'-phosphoadenosine 5'-phosphosulfate synthase (EC 2.7.1.25) can be constitutively expressed; a primary amine oxidase (EC 1.4.3.21) and decarboxylating cytochrome P450 can be expressed co-located or tethered; a puridine nucleotide transhydrogenase gene such as UdhA can be overexpressed; a glyceraldehyde-3P-dehydrogenase gene such as GapN can be overexpressed in the host organisms; a malic enzyme gene such as maeA or maeB is overexpressed in the host organism; a glucose-6-phosphate dehydrogenase gene such as zwf can be overexpressed in the host organism; a fructose 1,6 diphosphatase gene such as fbp can be overexpressed in the host organism; the efflux of butadiene across the cell membrane to the extracellular media can be enhanced or amplified by genetically engineering structural modifications to the cell membrane and/or the efflux of butadiene across the cell membrane to the extracellular media can be enhanced or amplified by genetically engineering an increase to any associated transporter activity for butadiene; oxygenases degrading butadiene to toxic intermediates such as 1,2-epoxy-3-butene and 1,2:3,4-diepoxybutane can be attenuated in the host organism.

More specifically, this document provides a first method of butadiene synthesis; the method includes introducing a first vinyl group into a first vinyl group acceptor compound using a dehydratase, a dehydrogenase, a isomerase, a synthase or a desaturase.

In a second method of butadiene synthesis, the method includes introducing a second vinyl group into a second vinyl group acceptor compound using a decarboxylating thioesterase, a decarboxylating cytochrome P450 or a dehydratase. The second method can further involve, prior to the introducing the second vinyl group, carrying out the first method, i.e., introducing a first vinyl group into a first vinyl group acceptor compound to produce the second vinyl group acceptor compound, using a dehydratase, a dehydrogenase, a isomerase, a synthase or a desaturase.

As used herein, a "first vinyl group acceptor compound" is a compound in any 1,3-butadiene synthetic pathway disclosed herein into which a first vinyl group corresponding to one of two vinyl groups in 1,3-butadiene is first introduced and is retained in any subsequent intermediate compounds in the pathway terminating in the production of 1,3-butadiene. Examples of first vinyl group acceptor compounds include pent-2-enoyl-[acp], 3-hydroxypropionyl-CoA, propanoyl-CoA, lactoyl-CoA, 5-hydroxypentanoyl-CoA, butan-2-ol, 2-buten-1-ol, 2-buten-1-ol diphosphate, 4-hydroxy-pentanoyl-CoA, and 4-hydroxy pent-2-enoyl-CoA.

As used herein, a "second vinyl group acceptor compound" is a compound in any 1,3-butadiene synthetic pathway disclosed herein that contains a first vinyl group corresponding to one of two vinyl groups in 1,3-butadiene and into which a second vinyl group corresponding to the second of the two vinyl groups in 1,3-butadiene is first introduced and is retained in any subsequent compounds in the pathway terminating in the production of 1,3-butadiene. It is noted that the introduction of the second vinyl group is most commonly the last step in the pathway, i.e., the step in which the reaction product is 1,3-butadiene. Examples of second vinyl group acceptor compounds include 3-sulphorylpent-4-enoyl-[acp], 3-phosphopent-4-enoyl-[acp], 3-phosphopent-4-enoyl-CoA, 3-sulphorylpent-4-enoyl-CoA, pent-4-enoate, and 3-buten-2-ol.

In the second method, the decarboxylating thioesterase introducing the second vinyl group can be an engineered enzyme having greater than 70% homology to the decarboxylating thioesterase from *Lyngbya majuscula* (CurM TE), *Pseudomonas entomophila*, *H. ochraceum*, *Synechococcus* PCC 7002, *Cyanothece* PCC 7424 or *Cyanothece* PCC 7822. In addition, the decarboxylating thioesterase introducing the second vinyl group can catalyse the hydrolysis of either 3-sulphorylpent-4-enoyl-[acp], 3-phosphopent-4-enoyl-[acp], 3-sulphorylpent-4-enoyl-CoA or 3-phosphopent-4-enoyl-CoA. Moreover, in the second method, following the introduction of the second vinyl group, the resulting compound can undergo spontaneous decarboxylation to butadiene. Also in the second method, the decarboxylating cytochrome P450 introducing the second vinyl group can be an engineered enzyme having greater than 70% homology to the decarboxylating cytochrome P450 from *Jeotgalicoccus* sp. ATCC 8456. Furthermore in the second method, the dehydratase introducing the second vinyl group can be an engineered enzyme having greater than 70% homology to linalool dehydratase (EC 4.2.1.127) from *Castellaniella defragrans*. In the second method, the decarboxylating thioesterase can convert 3-sulphorylpent-4-enoyl-[acp] or 3-phosphopent-4-enoyl-[acp] as substrate to butadiene. Also, in the second method, the decarboxylating cytochrome P450 can convert pent-4-enoic acid to butadiene and the hydrogen peroxide co-substrate required for the conversion of pent-4-enoic acid to butadiene can optionally be provided by the activity of a primary amine oxidase. Moreover in the second method, the dehydratase can convert 3-buten-2-ol to butadiene.

In the first method, whether carried out alone or prior to introducing a second vinyl group, the dehydratase (EC 4.2.1.-) enzyme introducing the first vinyl group can be an engineered enzyme having greater than 70% homology to the 5-aminovaleryl-CoA dehydratase from *C. viride*, linalool dehydratase (EC 4.2.1.127) or a dehydratase (EC 4.2.1.-) from species such as *Aquincola tertiaricarbonis* or *Methylibium petroleiphilum* PM1. Moreover, the dehydrogenase (e.g., an acyl-ACP dehydrogenase) introducing the first vinyl group can be an engineered enzyme having greater than 70% homology to the gene product of tcsD. In addition, in the first method, whether carried out alone or prior to introducing a second vinyl group, the desaturase/monooxygenase introducing the first vinyl group can be an engineered enzyme having greater than 70% homology to the gene product of MdpJ or cytochrome P450 CYT4 family. Furthermore, in the first method, whether carried out alone or prior to introducing a second vinyl group, the synthase introducing the first vinyl group can be an engineered enzyme have greater than 70% homology to 2-methyl-3-buten-2-ol synthase encoded by Tps-MBO1. Moreover, in the first method, whether carried out alone or prior to introducing a second vinyl group, the isomerase introducing the first vinyl group can be an engineered enzyme having greater than 70% homology to the isomerase from *Pseudomonas putida* catalyzing the conversion of 2-methyl-3-buten-2-ol to 2-methyl-3-buten-1-ol. Also, in the first method, whether carried out alone or prior to introducing a second vinyl group, the isomerase can convert 2-buten-1-ol to 3-buten-2-ol.

Any of the methods can involve a fermentation process using a host cell expressing an enzyme that catalyzes the introduction of a first vinyl group, an enzyme that catalyzes the introduction of a second vinyl group, or one or two enzymes that catalyze the introduction of a first and a second vinyl group. The host cell can be either of a prokaryote or a eukaryote. The prokaryote can be of the genus *Escherichia* such as *Escherichia coli*; of the genus *Clostridia* such as *Clostridium ljungdahlii*, *Clostridium autoethanogenum* or *Clostridium kluyveri*; of the genus *Corynebacteria* such as *Corynebacterium glutamicum*; of the genus *Cupriavidus* such as *Cupriavidus necator* or *Cupriavidus metallidurans*; of the genus *Pseudomonas* such as *Pseudomonas fluorescens* or *Pseudomonas putida*; of the genus *Bacillus* such as *Bacillus subtillis*; or of the genus *Rhodococcus* such as *Rhodococcus equi*. Moreover, the eukaryote can be of the genus *Aspergillus* such as *Aspergillus niger*; of the genus *Saccharomyces* such as *Saccharomyces cerevisiae*; of the genus *Pichia* such as *Pichia pastoris*; of the genus *Yarrowia* such as *Yarrowia lipolytica*; of the genus *Issatchenkia* such as *Issathenkia orientalis*; of the genus *Debaryomyces* such as *Debaryomyces hansenii*; of the genus *Arxula* such as *Arxula adenoinivorans*; or of the genus *Kluyveromyces* such as *Kluyveromyces lactis*. The fermentation process can include anaerobic, micro-aerobic or aerobic cell cultivation. In these methods, cell retention strategies using, for example, ceramic hollow fibre membranes can be employed to achieve and maintain a high cell density during fermentation. In addition, the principal carbon source fed to the fermentation can be derived from biological or non-biological feedstocks. Biological feedstock can be, or can be derived from, monosaccharides, disaccharides, hemicellulose such as levulinic acid and furfural, cellulose, lignocellulose, lignin, triglycerides such as glycerol and fatty acids, agricultural waste, or municipal waste. Non-biological feedstock can be, or can be derived from, natural gas, syngas, $CO_2/H_2$, methanol, ethanol, non-volatile residue (NVR), caustic wash from a cyclohexane oxidation processes, or other waste stream from the chemical or petrochemical industries.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DETAILED DESCRIPTION

Figure 1:
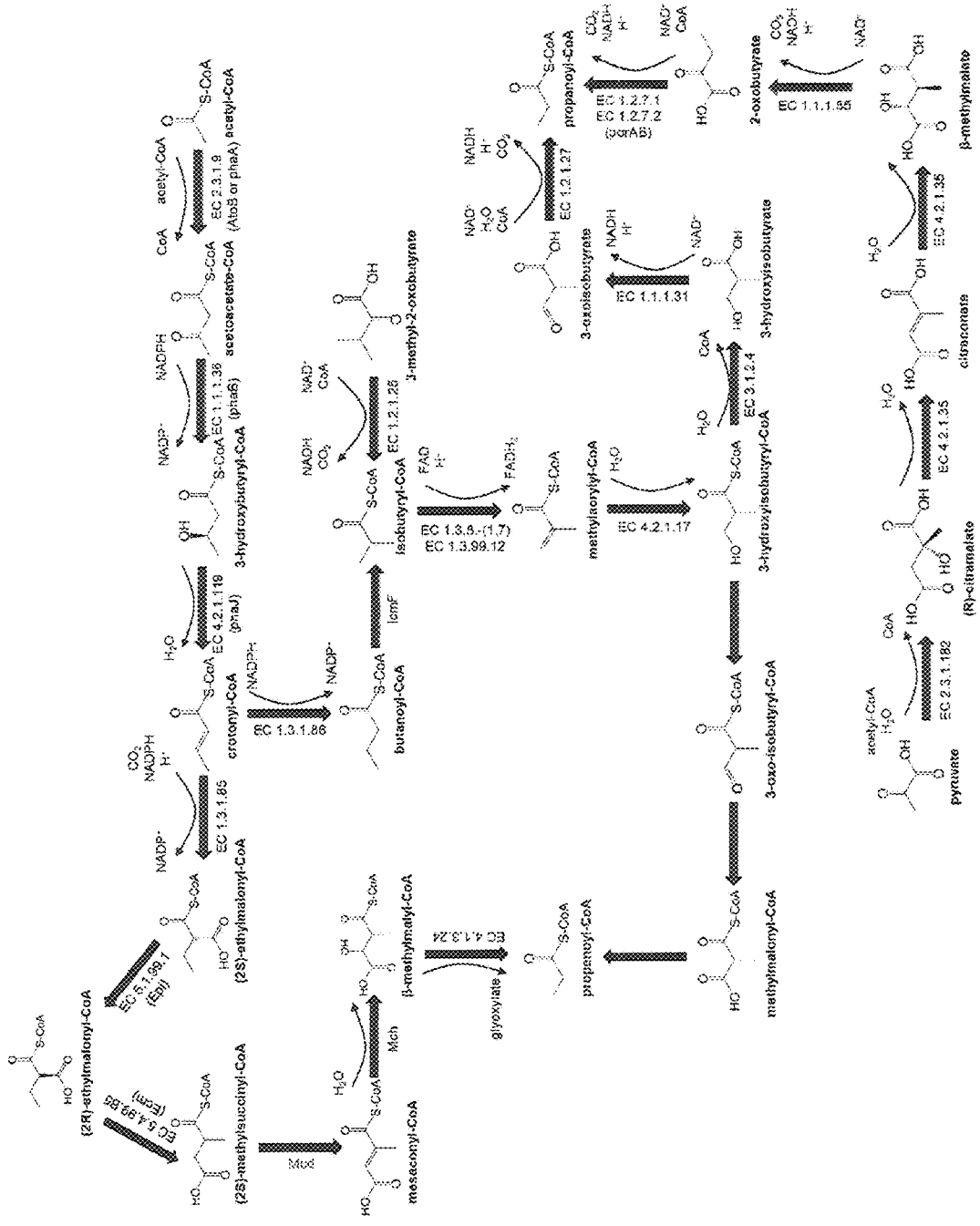
FIG. 1 is a schematic of biochemical pathways leading to the production of propanoyl-CoA from central metabolites.

The closest analogous compound synthesized by prokaryotes or eukaryotes is 2-methyl-1,3-butadiene (isoprene), given the short five carbon chain length and two vinyl groups. Isoprene may be synthesised via two routes leading to the precursor dimethylvinyl-PP, viz. the mevalonate or the non-mevalonate pathway (Kuzuyama, Biosci. Biotechnol. Biochem., 2002, 66(8), 1619-1627).

The mevalonate pathway incorporates a decarboxylase enzyme, mevalonate diphosphate decarboxylase (hereafter MDD), that generates the first vinyl-group in the precursors leading to isoprene (Kuzuyama, Biosci. Biotechnol. Biochem., 2002, 66(8), 1619-1627).

Enzymes with similar activity to mevalonate diphosphate decarboxylase (EC 4.1.1.33) may thus be earmarked as a candidate enzyme in the synthesis of butadiene from non-native substrates.

The chain termination enzymatic reactions in the polyketide synthesis of Curacin A involve sulphotransferase, encoded by CurM ST, and thioesterase, encoded by CurM TE, activity; mechanistically similar to the activity associated with MDD, thus earmarking the enzymes as candidates for the synthesis of butadiene from non-native substrates (Gehret et al., The Journal of Biological Chemistry, 2011, 286(16), 14445-14454).

However, the activity of the sulphotransferase and thioesterase domains in Curacin A biosynthesis has only been demonstrated for long (C12, C14) chain length substrate analogues (McCarthy et al., ACS Chem. Biol., 2012, 7, 1994-2003), teaching against using such sulphotransferase and thioesterase activity in the synthesis of butadiene from medium (e.g., C5) chain length precursors.

The enzyme encoded by $OleT_{JE}$ from the CYP152 cytochrome P450 family, introduces terminal vinyl groups into long chain fatty acids via decarboxylation (Rude et al., Appl. Environ. Microbiol., 2011, 77(5), 1718-1727).

The CYP152 fatty acid decarboxylase, $OleT_{JE}$, may thus be earmarked as a candidate enzyme in the synthesis of butadiene from non-native substrates.

Similar to the sulphotransferase and thioesterase activity terminating Curacin A biosynthesis, $OleT_{JE}$ has specificity for long chain length fatty acids (C18-C20) with low activity for C15 chain length fatty acids (Rude et al., Appl. Environ. Microbiol., 2011, 77(5), 1718-1727), teaching against using $OleT_{JE}$ in the synthesis of butadiene from medium (e.g., C5) chain length precursors.

In addition to decarboxylase activity, microorganisms can generate vinyl groups in metabolites typically via dehydratase, ammonia lyase or desaturase activity. However, these enzyme activities rarely catalyse the formation of terminal vinyl groups. Dehydratases and ammonia lyases typically accept fatty acid analogues that have activated hydrogen atoms or aromatic compounds, where the aromatic ring serves as an electron withdrawing group. Desaturases predominate in fatty acid synthesis, generating unsaturated bonds at fixed non-terminal positions along long chain fatty acids. Therefore, the associated enzymatic activity of these enzymes teaches against their use for the generation of terminal vinyl groups in short or medium chain carbon metabolites leading to the synthesis of butadiene.

In particular, this document provides enzymes, non-natural pathways, cultivation strategies, feedstocks, host microorganisms and attenuations to the host's biochemical network, which generate two terminal vinyl groups in four and five carbon chain metabolites leading to the synthesis of 1,3 butadiene (sometimes referred to as "butadiene" herein) from central precursors or central metabolites. As used herein, the term "central precursor" is used to denote any metabolite in any metabolic pathway shown herein leading to the synthesis of butadiene. The term "central metabolite" is used herein to denote a metabolite that is produced in all microorganisms to support growth.

As such, host microorganisms described herein can include endogenous pathways that can be manipulated such that butadiene can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host. Within an engineered pathway, the enzymes can be from a single source, i.e., from one species, or can be from multiple sources, i.e., different species. Nucleic acids encoding the enzymes described herein have been identified from various organisms and are readily available in publicly available databases such as GenBank or EMBL.

An the enzymes described herein that can be used for butadiene production can have at least 70% sequence identity (homology) (e.g., at least 75%, 80%, 85%, 90%, 95%, 97%, 98%, 99%, or 100%) to the amino acid sequence of the corresponding wild-type enzyme. The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine (SEQ ID NO: 7; corresponding nucleic acid sequence set forth in SEQ ID NO: 8)), hemagluttanin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Engineered (or recombinant) hosts can naturally express none or some (e.g., one or more, two or more, three or more, four or more, five or more, or six or more) of the enzymes of the pathways described herein. Endogenous genes of the engineered hosts also can be disrupted to prevent the formation of undesirable metabolites or prevent the loss of intermediates in the pathway through other enzymes acting on such intermediates. Engineered hosts can be referred to as engineered host cells, engineered cells, recombinant hosts recombinant host cells, or recombinant cells. Thus, as described herein recombinant hosts can include nucleic acids encoding one or more of a dehydrogenase, a desaturase, a cytochrome P450, a decarboxylating thioesterase, a sulphotransferase, a phosphotransferase, an acyl [acyl carrier protein (acp)] dehydrogenase, a dehydratase, or a hydratase as described in more detail below.

In addition, the production of butadiene can be performed in vitro using the isolated enzymes described herein, using a lysate (e.g., a cell lysate) from a host microorganism as a source of the enzymes, or using a plurality of lysates from different host microorganisms as the source of the enzymes.

4.1 Enzymes Generating the First Terminal Vinyl Group in the Biosynthesis of Butadiene As depicted in FIGS. 2-6, the first vinyl group can be formed in pent-2-enoyl-[acp], 3-hydroxypropionyl-CoA, propanoyl-CoA, lactoyl-CoA, 5-hydroxypentanoyl-CoA, butan-2-ol, 2-buten-1-ol, 2-buten-1-ol diphosphate, 4-hydroxy-pentanoyl-CoA, or 4-hydroxy pent-2-enoyl-CoA.

In some embodiments, the first vinyl group leading to the synthesis of butadiene is enzymatically formed in pent-2-enoyl-[acp] by an acyl-[acp] dehydrogenase such as the gene product of TcsD to produce 2,4-pentadienoyl-[acp]. (e.g., FIG. 2). The gene product of the acyl-[acp] dehydrogenase TcsD desaturates the terminal methylene of pent-2-enoyl-[acp] to 2,4-pentadienoyl-[acp] (Mo et al., *J. Am. Chem. Soc.*, 2011, 133(4), 976-985).

In some embodiments, the first vinyl group leading to the synthesis of butadiene is enzymatically formed in propanoyl-CoA, lactoyl-CoA, or 3-hydroxypropionyl-CoA by butyryl-CoA dehydrogenase (EC 1.3.8.1), medium-chain acyl-CoA dehydrogenase (EC 1.3.8.7), 2-methylacyl-CoA dehydrogenase (EC 1.3.99.12), lactoyl-CoA dehydratase (EC 4.2.1.54) or 3-hydroxypropionyl-CoA dehydratase (EC 4.2.1.116) to produce propenoyl-CoA. (e.g., FIG. 3).

In some embodiments, the first vinyl group leading to the synthesis of butadiene is enzymatically formed in 5-hydroxypentanoyl-CoA (via 5-hydroxy-pent-2-enoyl-CoA) by a 5-hydroxyvaleryl-CoA dehydratase (EC 4.2.1.-). (e.g., FIG. 4). The dehydration of 5-hydroxyvalerate by 5-hydroxyvaleryl-CoA dehydratase to 2,4-pentadienoyl-CoA has been characterized from *Clostridium viride* (Eikmanns and Buckel, *Eur. J. Biochem.*, 1991, 197, 661-668).

In some embodiments, the first vinyl group leading to the synthesis of butadiene is formed in 2-butanol (butan-2-ol) by a desaturase such as the gene product of MdpJ to produce 3-buten-2-ol. (e.g., FIG. 5).

In some embodiments, the first vinyl group leading to the synthesis of butadiene is formed in 2-buten-1-ol by an isomerase such as isolated from *Pseudomonas putida* classified under EC 5.4.4.—to produce 3-buten-2-ol. (e.g., FIG. 5)

Figure 5:
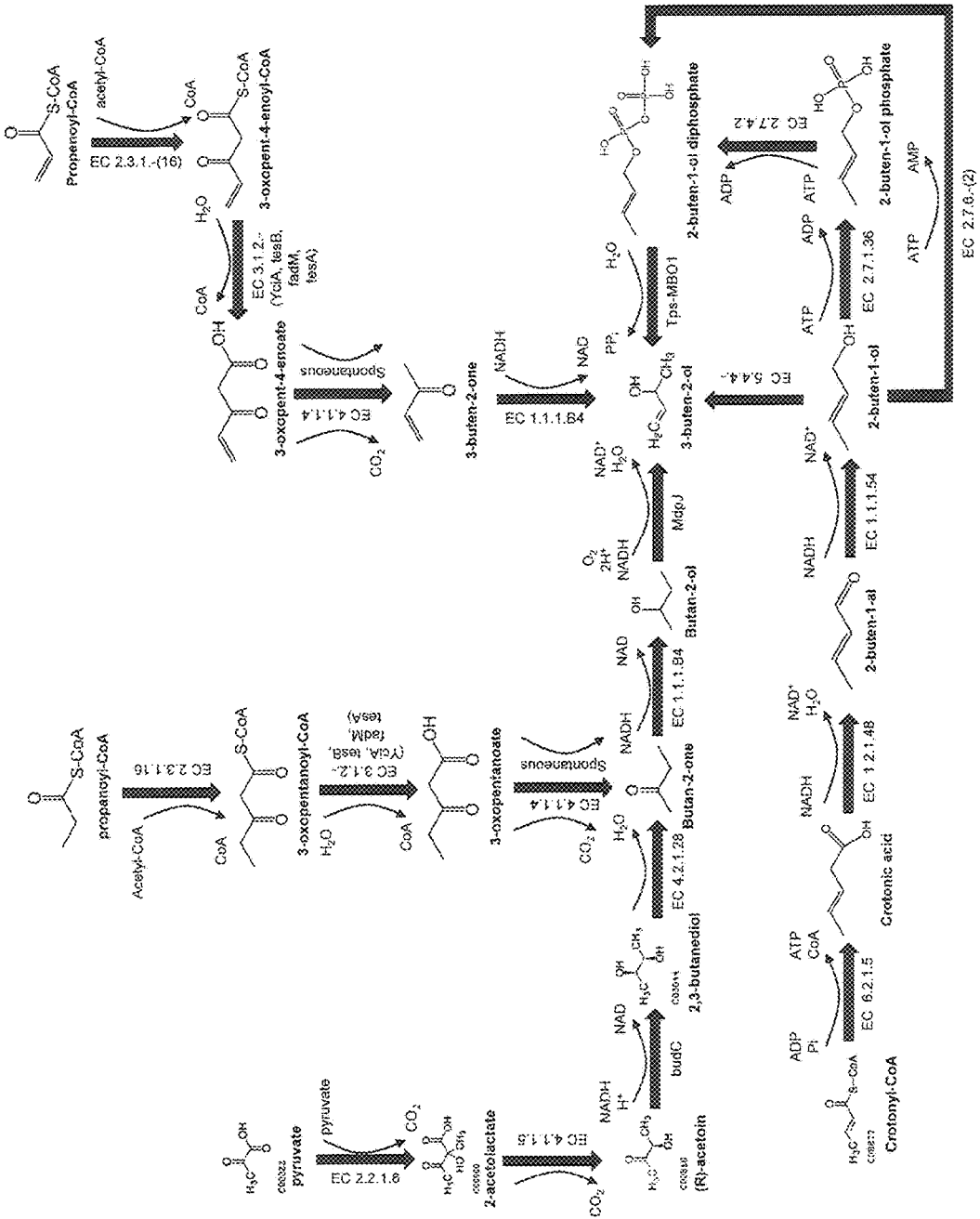
FIG. 5 is a schematic of biochemical pathways leading to the production of 3-buten-2-ol using pyruvate or crotonyl-CoA as a central precursor.

In some embodiments, the first vinyl group leading to the synthesis of butadiene is formed in 2-buten-1-ol diphosphate by a 2-methyl-3-buten-2-ol synthase such as the gene product of Tps-MB01 to produce 3-buten-2-ol. (FIG. 5).

Figure 6:
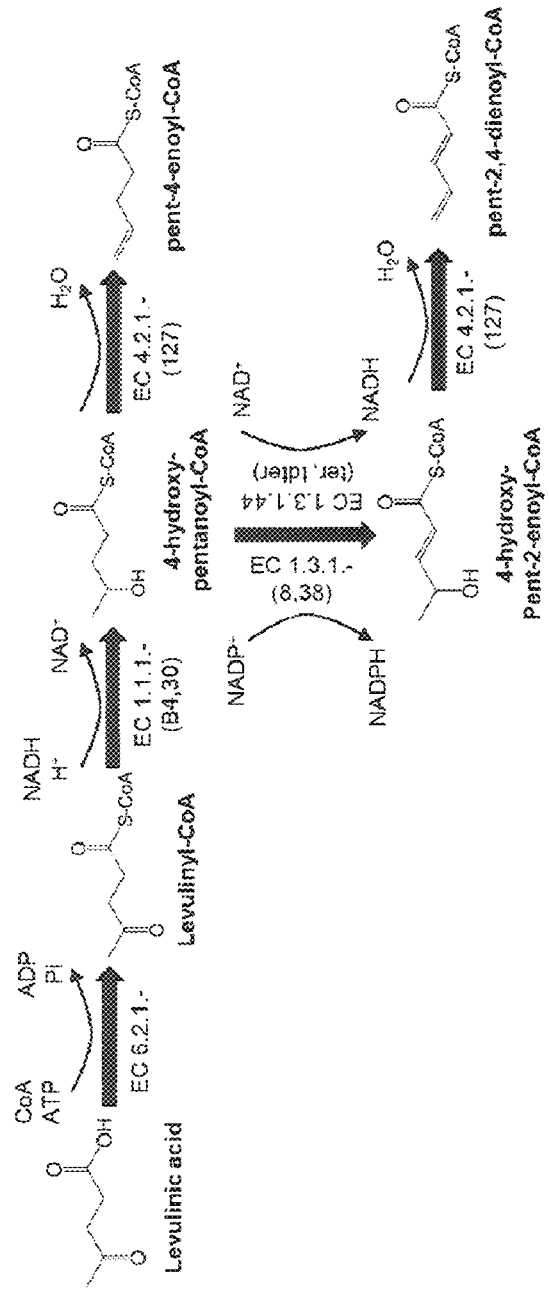
FIG. 6 is a schematic of biochemical pathways leading to the production of pent-4-enoyl-CoA or pent-2,4-enoyl-CoA as central precursor.

In some embodiments, the first vinyl leading to the synthesis of butadiene is formed in 4-hydroxy-pentanoyl-CoA by a dehydratase such as linalool dehydratase classified in EC 4.2.1.127 or a dehydratase classified under EC 4.2.1.—(such as one isolated from species such as *Aquincola tertiaricarbonis* or *Methylibium petroleiphilum* PM1). (FIG. 6).

In some embodiments, the first vinyl group leading to the synthesis of butadiene is formed in 4-hydroxy-pent-2-enoyl-CoA by a dehydratase such as linalool dehydratase classified in EC 4.2.1.127 or a dehydratase classified under EC 4.2.1.—(such as one isolated from species such as *Aquincola tertiaricarbonis* or *Methylibium petroleiphilum* PM1). (FIG. 6)

Figure 7:
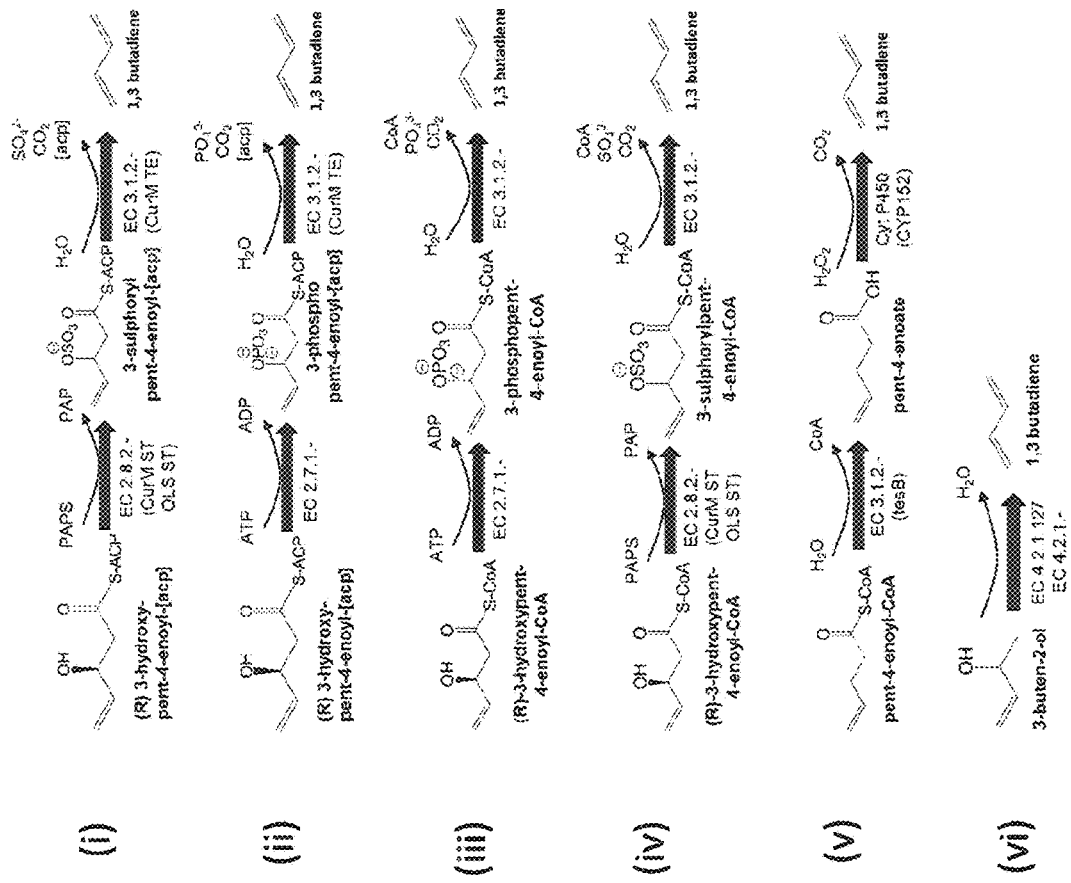
FIG. 7 is a schematic of biochemical pathways leading to the production of butadiene using a sulphotransferase followed by a decarboxylating thioesterase ((i) and (iv)), phosphotransferase followed by decarboxylating thioesterase ((ii) and (iii)), a decarboxylating cytochrome P450 in the CYP152 family (v), linalool dehydratase or a dehydratase classified under EC 4.2.1.—(such as one isolated from species such as *Aquincola tertiaricarbonis* or *Methylibium petroleiphilum* PM1) (vi).

4.2 Enzymes Generating the Second Terminal Vinyl Group in the Biosynthesis of Butadiene As depicted in FIG. 7, the second vinyl group can be enzymatically formed using a decarboxylating thioesterase, a decarboxylating cytochrome P450 or a dehydratase.

In some embodiments, the second vinyl group leading to the synthesis of butadiene is formed by a decarboxylating thioesterase such as the gene product of CurM TE. (e.g., (i)-(iv) in FIG. 7).

In some embodiments, the second vinyl group leading to the synthesis of butadiene is enzymatically formed by a decarboxylating cytochrome P450 in the CYP152 family. (e.g., (v) in FIG. 7).

In some embodiments, the second vinyl group leading to the synthesis of butadiene is enzymatically formed by a dehydratase such as linalool dehydratase classified in EC 4.2.1.127 or a dehydratase classified under EC 4.2.1.—(such as one isolated from species such as *Aquincola tertiaricarbonis* or *Methylibium petroleiphilum* PM1). (e.g., (vi) in FIG. 7).

Linalool may be regarded as 3-buten-2-ol substituted with an isohexenyl R-group at the alpha position. The dehydration of linalool to myrcene is favored thermodynamically and likely proceeds via deprotonation, where the R-group has no mechanistic role (Bordkorb et al., *J. Biol. Chem.*, 2010, 285(40), 30436-30442).

Figure 2:
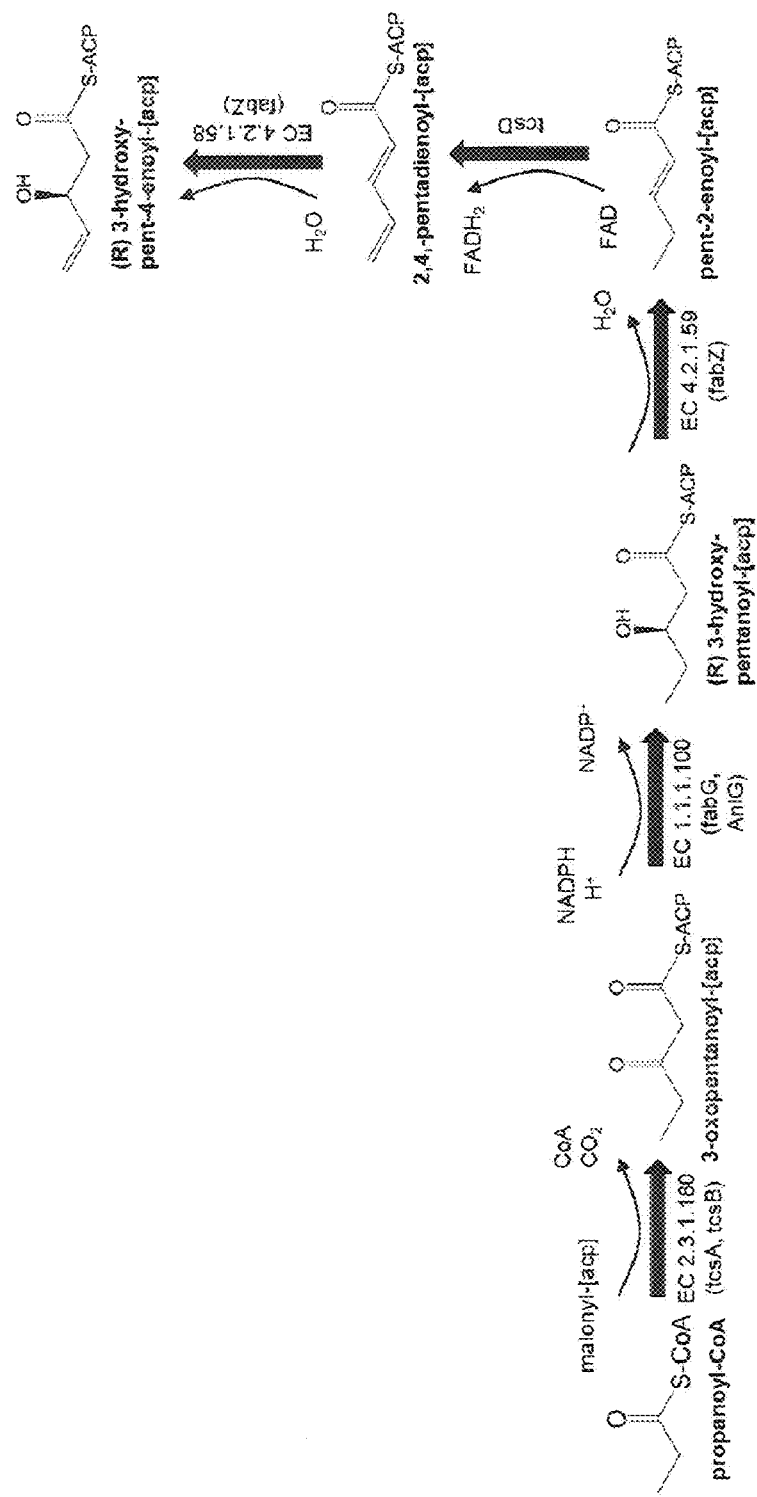
FIG. 2 is a schematic of biochemical pathways leading to the production of (R)-3-hydroxypent-4-enoyl-[acp] using propanoyl-CoA as a central precursor.

4.3 Biochemical Pathways 4.3.1 Pathways using 2,4-pentadienoyl-[acp] as Central Precursor to Butadiene In some embodiments, 2,4-pentadienoyl-[acp] is the central precursor leading to the synthesis of butadiene (FIG. 2).

In some embodiments, 2,4-pentadienoyl-[acp] can be produced by forming a first vinyl group in pent-2-enoyl-[acp] using an acyl-[acp] dehydrogenase such as encoded by tcsD (FIG. 2) The pent-2-enoyl-[acp] can be produced by converting (R)-3-hydroxypentanoyl-[acp] using a 3-hydroxyacyl-[acp] dehydratase classified under EC 4.2.1.59 such as encoded by fabZ (FIG. 2) The (R)-3-hydroxypentanoyl-[acp] can be produced by converting (R)-3-oxopentanoyl-[acp] using a 3-oxoacyl-[acp] reductase classified in EC 1.1.1.100 such as encoded by fabG or AnlG (FIG. 2) The (R)-3-oxopentanoyl-[acp] can be produced by converting propanoyl-CoA using a β-ketoacyl-[acp] synthase such as encoded by tcsA and tcsB (FIG. 2). The propanoyl-CoA can be produced via a number of pathways (FIG. 1).

In some embodiments, butadiene is synthesized from 2,4-pentadienoyl-[acp] by conversion to (R)-3-hydroxypent-4-enoyl-[acp] by 3-hydroxyacyl-[acp] dehydratase classified under EC 4.2.1.59 such as encoded by fabZ (FIG. 2); followed by conversion to 3-sulphorylpent-4-enoyl-[acp] by sulphotransferase classified under EC 2.8.2.—such as encoded by CurM ST or OLS ST (FIG. 7); followed by conversion to butadiene by decarboxylating thioesterase such as encoded by CurM TE. (FIG. 7).

In some embodiments, butadiene is synthesized from 2,4-pentadienoyl-[acp] by conversion to (R)-3-hydroxypent-4-enoyl-[acp] by 3-hydroxyacyl-[acp] dehydratase classified under EC 4.2.1.59 such as encoded by fabZ (FIG. 2); followed by conversion to 3-phosphopent-4-enoyl-[acp] by phosphotransferase classified under EC 2.7.1.—(FIG. 7); followed by conversion to butadiene by decarboxylating thioesterase such as encoded by CurM TE. (FIG. 7).

4.3.2 Pathways Using Propenoyl-CoA as Central Precursor to Butadiene

Figure 3:
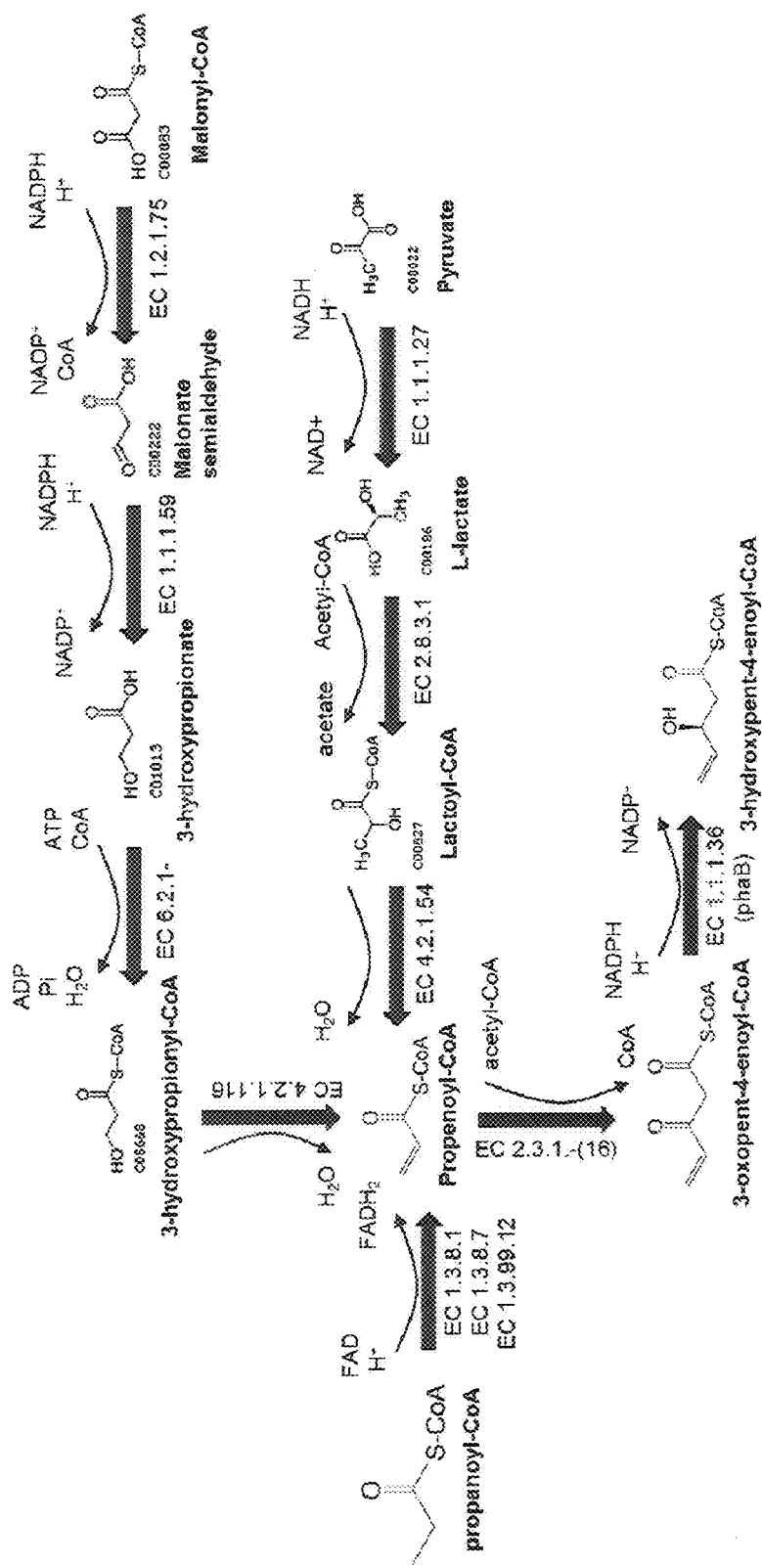
FIG. 3 is a schematic of biochemical pathways leading to the production of 3-hydroxypent-4-enoyl-CoA using propenyl-CoA as a central precursor.

In some embodiments, propenoyl-CoA is the central precursor leading to the synthesis of butadiene (FIG. 3).

In some embodiments, propenoyl-CoA is synthesized from propanoyl-CoA by butyryl-CoA dehydrogenase (classified under EC 1.3.8.1), medium-chain acyl-CoA dehydrogenase (classified under EC 1.3.8.7) or 2-methylacyl-CoA dehydrogenase (classified under EC 1.3.99.12). (e.g., FIG. 3).

In some embodiments, propenoyl-CoA is synthesized from the central metabolite, pyruvate, by conversion of pyruvate to L-lactate by L-lactate dehydrogenase (classified under EC 1.1.1.27); followed by conversion to lactoyl-CoA by proprionate CoA-transferase (classified under EC 2.8.3.1); followed by conversion to propenoyl-CoA by lactoyl-CoA dehydratase (classified under EC 4.2.1.54). (e.g., FIG. 3).

In some embodiments, propenoyl-CoA is synthesized from the central metabolite, malonyl-CoA, by conversion to conversion to 3-hydroxypropionate by 3-hydroxypropionate dehydrogenase (classified under EC 1.1.1.59); followed by conversion to 3-hydroxypropionyl-CoA by 3-hydroxyisobutyryl-CoA hydrolase (classified under EC 6.2.1); followed by conversion to propenoyl-CoA by 3-hydroxypropionyl-CoA dehydratase (classified under EC 4.2.1.116). (e.g., FIG. 3).

In some embodiments, butadiene is synthesized from propenoyl-CoA by conversion to 3-oxopent-4-enoyl-CoA by β-ketothiolase such as that classified under EC 2.3.1.16; followed by conversion to (R)-3-hydroxypent-4-enoyl-CoA by acetoacetyl-CoA reductase (classified under EC 1.1.1.36) such as the gene product of phaB (FIG. 3); followed by conversion to 3-sulphorylpent-4-enoyl-CoA by sulphotransferase classified under EC 2.8.2.—such as encoded by CurM ST or OLS ST; followed by conversion to butadiene by decarboxylating thioesterase such as encoded by CurM TE. (FIG. 7).

In some embodiments, butadiene is synthesized from propenyl-CoA by conversion to 3-oxopent-4-enoyl-CoA by β-ketothiolase such as that classified under EC 2.3.1.16 (FIG. 3); followed by conversion to (R)-3-hydroxypent-4-enoyl-CoA by acetoacetyl-CoA reductase (classified under EC 1.1.1.36) such as the gene product of phaB (FIG. 3); followed by conversion to 3-phosphopent-4-enoyl-CoA by phosphotransferase classified under EC 2.7.1.—(FIG. 7); followed by conversion to butadiene by decarboxylating thioesterase such as encoded by CurM TE. (FIG. 7).

4.3.3 Pathway Using 2,4-Pentadienoyl-CoA as Central Precursor to Butadiene

Figure 4:
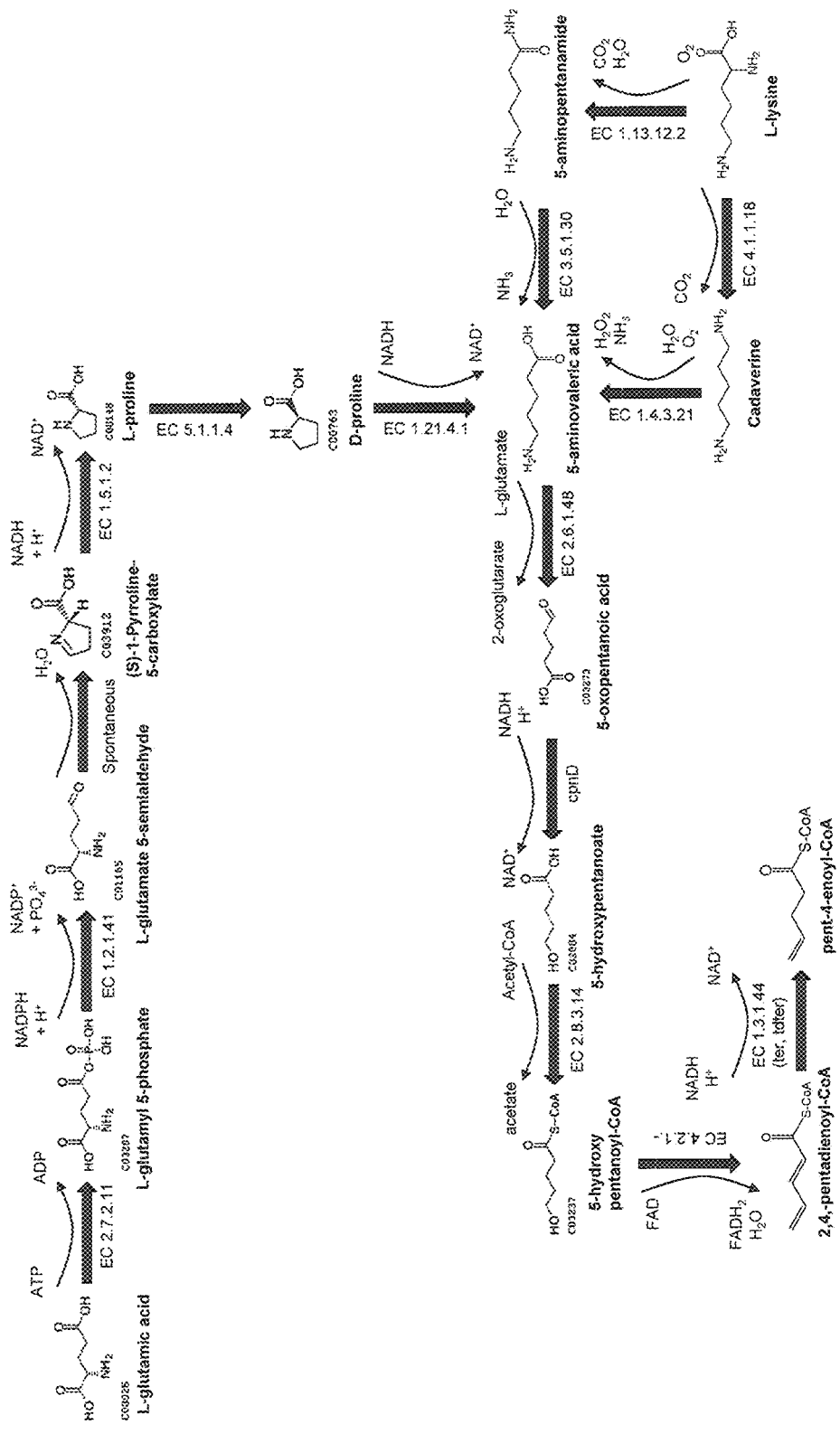
FIG. 4 is a schematic of biochemical pathways leading to the production of pent-4-enoyl-CoA using 5-aminovalerate (5-aminovaleric acid) as a central precursor.

In some embodiments, 2,4-pentadienoyl-CoA is the central precursor leading to the synthesis of butadiene (FIG. 4).

In some embodiments, 2,4-pentadienoyl-CoA is synthesized from 5-aminovalerate (5-aminovaleric acid) by conversion to 5-oxopentanoate (5-oxopentanoic acid) by a 5-aminovalerate transaminase (classified under EC 2.6.1.48); followed by conversion to 5-hydroxypentanoate by a 5-hydroxyvalerate dehydrogenase such as the gene product of cpnD or a dehydrogenase from Clostridium viride; followed by conversion to 5-hydroxypentanoyl-CoA by a 5-hydroxypentanoate CoA-transferase (classified under EC 2.8.3.14); followed by conversion to 2,4-pentadienoyl-CoA by a 5-hydroxyvaleryl-CoA dehydratase (classified under EC 4.2.1.—) (e.g., that from Clostridium viride). (e.g., FIG. 4).

In some embodiments, 2,4-pentadienoyl-CoA is synthesized from levulinic acid by conversion to levulinyl-CoA by CoA-ligase (classified under EC 6.2.1.—); followed by conversion to 4-hydroxypentanoyl-CoA by secondary alcohol dehydrogenase (classified under EC 1.1.1.B4) or 3-hydroxybutanoate oxidoreductase (classified under EC 1.1.1.30); followed by conversion to 4-hydroxypent-2-enoyl-CoA by reversible trans-2-enoyl-CoA reductase (classified under EC 1.3.1.—(8,38,44); followed by conversion to 2,4-pentadienoyl-CoA by a dehydratase such as linalool dehydratase (classified in EC 4.2.1.127) or a dehydratase classified under EC 4.2.1.—(such as one isolated from species such as Aquincola tertiaricarbonis or Methylibium petroleiphilum PM1). (FIG. 6).

In some embodiments, butadiene is synthesized from 2,4-pentadienoyl-CoA by conversion to 4-pentenoyl-CoA (pent-4-enoyl-CoA) by 5-hydroxyvaleryl-CoA dehydratase (classified under EC 1.3.1.44) (e.g., that from Clostridium viride) (FIG. 4); followed by conversion to butadiene by decarboxylating cytrochrome P450 in the CYP152 family. (FIG. 7).

4.3.4 Pathway Using Pent-4-Enoyl-CoA as Central Precursor to Butadiene without First Forming 2,4-Pentadienoyl-CoA In some embodiments, pent-4-enoyl is the central precursor leading to the synthesis of butadiene without first forming 2,4-pentadienoyl-CoA.

In some embodiments, pent-4-enoyl-CoA is synthesized from levulinic acid by conversion to levulinyl-CoA by a CoA ligase (classified under EC 6.2.1.—); followed by conversion to 4-hydroxy-pentanoyl-CoA by a secondary alcohol dehydrogenase classified under EC 1.1.1.B4 such or a 3-hydroxy butanoate oxidoreductase classified under EC 1.1.1. 30; followed by conversion to pentanoyl-4-enoyl-CoA by a dehydratase such as linalool dehydratase (classified in EC 4.2.1.127) or a dehydratase classified under EC 4.2.1.—(such as one isolated from species such as Aquincola tertiaricarbonis or Methylibium petroleiphilum PM1). (FIG. 6).

In some embodiments, butadiene is synthesized from 4-pentenoyl-CoA (pent-4-enoyl-CoA) by decarboxylating cytrochrome P450 in the CYP152 family. (FIG. 7).

4.3.5 Pathway Using 3-buten-2-ol as Central Precursor to Butadiene

In some embodiments, 3-buten-2-ol is the central precursor leading to the synthesis of butadiene. (FIG. 5).

In some embodiments, 2-buten-1-ol is synthesized from crotonyl-CoA by conversion to crotonic acid by a succinate-CoA ligase (classified under EC 6.2.1.5); followed by conversion to 2-butenl-al by a long-chain-aldehyde dehydrogenase (classified under EC 1.2.1.48); followed by conversion to 2-buten-1-ol by an allyl-alcohol dehydrogenase (classified under EC 1.1.1.54). See FIG. 5.

In some embodiments, 3-buten-2-ol is synthesized from 2-buten-1-ol by conversion to 2-buten-1-ol phosphate by a mevalonate kinase (classified under EC 2.7.1.36); followed by conversion to 2-buten-1-ol diphosphate by a phosphomevalonate kinase (EC 2.7.4.2); followed by conversion to 3-buten-2-ol by a 2-methyl-3-buten-2-ol synthase such as that encoded by Tps-MBO1. (e.g., FIG. 5).

In some embodiments, 3-buten-2-ol is synthesized from 2-buten-1-ol by conversion to 2-buten-1-ol diphosphate by a diphosphotransferases such as a thiamine diphosphokinase (classified under EC 2.7.6.2); followed by conversion to 3-buten-2-ol by a 2-methyl-3-buten-2-ol synthase such as encoded by Tps-MBO1. (e.g., FIG. 5).

In some embodiments, 3-buten-2-ol is synthesized from the central metabolite, pyruvate, by conversion of pyruvate to 2-acetolactate by an acetolactate synthase (classified under EC 2.2.1.6); followed by conversion to (R)-acetoin by an acetolactate decarboxylase (classified under EC 4.1.1.5); followed by conversion to 2,3 butanediol by a (R,S)-butanediol dehydrogenase such as encoded by budC; followed by conversion to butanone (butan-2-one) by a propanediol dehydratase (classified under EC 4.2.1.28); followed by conversion to 2-butanol (butan-2-ol) by a (R)-specific secondary alcohol dehydrogenase (classified under EC 1.1.1.B4); followed by conversion to 3-buten-2-ol by a desaturase or a monooxygenase such as the gene product of MdpJ or cytochrome P450 in, for example, the CYP4 family. (e.g., FIG. 5).

In some embodiments, 3-buten-2-ol is synthesized from the central precursor, propanoyl-CoA, by conversion of propanoyl-CoA to 3-oxopentanoyl-CoA using a β-ketothiolase classified under EC 2.3.1.16; followed by conversion to 3-oxopentanoate by thioesterase classified under EC 3.1.2.—such as the gene product of YciA, tesB, tesA or fadM; followed by conversion to 2-butanone (butan-2-one) by acetoacetate decarboxylase classified under EC 4.1.1.4; followed by conversion to 2-butanol (butan-2-ol) by a (R)-specific secondary alcohol dehydrogenase (EC 1.1.1.B4); followed by conversion to 3-buten-2-ol by a desaturase or a monooxygenase such as the gene product of MdpJ or cytochrome P450 in, for example, the CYP4 family. (e.g., FIG. 5).

In some embodiments, 3-buten-2-ol is synthesized from the central precursor, propenoyl-CoA, by conversion of propenoyl-CoA to 3-oxopent-4-enoyl-CoA using a β-ketothiolase classified under EC 2.3.1.—(such as that classified under EC2.3.1.16); followed by conversion to 3-oxopent-4-enoate by thioesterase classified under EC 3.1.2.—such as the gene product of YciA, tesB, tesA or fadM; followed by conversion to 3-buten-2-one by acetoacetate decarboxylase classified under EC 4.1.1.4; followed by conversion to 3-buten-2-ol by a (R)-specific secondary alcohol dehydrogenase (EC 1.1.1.B4). (e.g., FIG. 5).

In some embodiments, 3-buten-2-ol is synthesized from 2-buten-1-ol by an isomerase classified under EC 5.4.4.—such as that isolated from *Pseudomonas putida*. (e.g., FIG. 5).

In some embodiments, butadiene is synthesized from 3-buten-2-ol by linalool dehydratase in enzyme class EC 4.2.1.127 or a dehydratase classified under EC 4.2.1.—(such as one isolated from species such as *Aquincola tertiaricarbonis* or *Methylibium petroleiphilum* PM1). (e.g., FIG. 7).

4.4 Cultivation Strategy

In some embodiments, butadiene is biosynthesized in a recombinant host using a fermentation strategy that can include anaerobic, micro-aerobic or aerobic cultivation of the recombinant host.

Pathways in the synthesis of butadiene that incorporate enzymes requiring molecular oxygen and enzymes characterized in vitro as being oxygen sensitive require a micro-aerobic cultivation strategy maintaining a low dissolved oxygen concentration, whilst maintaining sufficient oxygen transfer to prevent substrate oxidation controlled conditions (Chayabatra & Lu-Kwang, *Appl. Environ. Microbiol.*, 2000, 66(2), 493 0 498).

In some embodiments, a cell retention strategy using, for example, ceramic hollow fiber membranes is employed to achieve and maintain a high cell density during either fed-batch or continuous fermentation in the synthesis of butadiene.

In some embodiments, the principal carbon source fed to the fermentation in the synthesis of butadiene derives from biological or non-biological feedstocks.

In some embodiments, the biological feedstock is, includes, or derives from, monosaccharides, disaccharides, lignocellulose, hemicellulose, cellulose, lignin such as levulinic acid and furfural, lignin, triglycerides such as glycerol and fatty acids, agricultural waste or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida* and *Yarrowia lipolytica* (Lee et al., Appl. Biochem. Biotechnol., 2012, 166, 1801-1813; Yang et al., *Biotechnology for Biofuels*, 2012, 5:13; Meijnen et al., *Appl. Microbiol. Biotechnol.*, 2011, 90, 885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, *Journal of Biotechnology*, 2011, 155, 2011, 293-298; Martin and Prather, *Journal of Biotechnology*, 2009, 139, 61-67).

The efficient catabolism of lignin-derived aromatic compounds such benzoate analogues has been demonstrated in several microorganisms such as *Pseudomonas putida, Cupriavidus necator* (Bugg et al., *Current Opinion in Biotechnology*, 2011, 22, 394-400; Pérez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7), 2419-2428).

The efficient utilization of fermentable sugars such as monosaccharides and disaccharides derived from cellulosic, hemicellulosic, cane and beet molasses, cassava, corn and other argricultural sources has been demonstrated for several microorganism such as *Escherichia coli, Corynebacterium glutamicum* and *Lactobacillus delbrueckii* and *Lactococcus lactis* (see, e.g., Hermann et al, *Journal of Biotechnology*, 2003, 104, 155-172; Wee et al., *Food Technol. Biotechnol.*, 2006, 44(2), 163-172; Ohashi et al., *Journal of Bioscience and Bioengineering*, 1999, 87(5), 647-654).

The efficient utilization of furfural, derived from a variety of agricultural lignocellulosic sources, has been demonstrated for *Cupriavidus necator* (Li et al., *Biodegradation*, 2011, 22, 1215-1225).

In some embodiments, the non-biological feedstock is, or derives from, natural gas, syngas, $CO_2/H_2$, methanol, ethanol, non-volatile residue (NVR) or a caustic wash waste stream from cyclohexane oxidation processes.

The efficient catabolism of methanol has been demonstrated for the methylotropic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium ljungdahlii* and *Clostridium autoethanogenum* (Kopke et al., *Applied and Environmental Microbiology*, 2011, 77(15), 5467-5475).

The efficient catabolism of the non-volatile residue waste stream from cyclohexane processes has been demonstrated for numerous microorganisms, such as *Delftia acidovorans* and *Cupriavidus necator* (Ramsay et al., *Applied and Environmental Microbiology*, 1986, 52(1), 152-156).

In some embodiments, the host microorganism is a prokaryote. For example, the prokaryote can be from the genus *Escherichia* such as *Escherichia coli*; from the genus *Clostridia* such as *Clostridium ljungdahlii, Clostridium autoethanogenum* or *Clostridium kluyveri*; from the genus *Corynebacteria* such as *Corynebacterium glutamicum*; from the genus *Cupriavidus* such as *Cupriavidus necator* or

*Cupriavidus metallidurans*; from the genus *Pseudomonas* such as *Pseudomonas fluorescens, Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. Such prokaryotes also can be sources of genes to construct recombinant host cells described herein that are capable of producing butadiene.

In some embodiments, the host microorganism is a eukaryote. Eukaryotes can be, for example, fungi (e.g., filamentous fungi or yeasts). For example, the eukaryote can be from the genus *Aspergillus* such as *Aspergillus niger*; from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing butadiene.

4.5 Metabolic Engineering

The present document provides methods involving less than all the steps described for all the above pathways. Such methods can involve, for example, one, two, three, four, five, six, seven, eight, nine, ten, or more of such steps. Where less than all the steps are included in such a method, the first step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined in section 4.3 are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined in section 4.3 are gene dosed, i.e., overexpressed, into the resulting genetically modified organism via episomal or chromosomal integration approaches.

In some embodiments, genome-scale system biology techniques such as Flux Balance Analysis are utilized to devise genome scale attenuation or knockout strategies for directing carbon flux to butadiene.

Attenuation strategies include, but are not limited to; the use of transposons, homologous recombination (double cross-over approach), mutagenesis, enzyme inhibitors and RNAi interference.

In some embodiments, fluxomic, metabolomic and transcriptomal data are utilized to inform or support genome-scale system biology techniques, thereby devising genome scale attenuation or knockout strategies in directing carbon flux to butadiene.

In some embodiments requiring intracellular availability of propanoyl-CoA or propenoyl-CoA for butadiene synthesis, genes (e.g., endogenous genes) encoding enzymes catalyzing the hydrolysis of propionyl-CoA and acetyl-CoA can be attenuated in the host organism.

In some embodiments requiring the intracellular availability of propanoyl-CoA or propenoyl-CoA for butadiene synthesis, genes (e.g., endogenous genes) encoding enzymes consuming propanoyl-CoA via the methyl-citrate cycle can be attenuated in the host organism (Upton and Mckinney, *Microbiology*, 2007, 153, 3973-3982).

In some embodiments requiring the intracellular availability of propanoyl-CoA or propenoyl-CoA for butadiene synthesis, genes (e.g., endogenous genes) encoding enzymes consuming propanoyl-CoA to pyruvate can be attenuated in the host organism.

In some embodiments requiring the intracellular availability of propanoyl-CoA or propenoyl-CoA for butadiene synthesis, genes (e.g., endogenous genes) encoding enzymes consuming propanoyl-CoA to malonyl-CoA can be attenuated in the host organism.

In some embodiments requiring the intracellular availability of propanoyl-CoA or propenoyl-CoA via L-threonine as central metabolite for butadiene synthesis, a feedback-resistant threonine deaminase is genetically engineered into the host organism (Tseng et al., *Microbial Cell Factories*, 2010, 9:96).

In some embodiments requiring condensation of acetyl-CoA and propanoyl-CoA/propenoyl-CoA for butadiene synthesis, the genes (e.g., endogenous genes) encoding β-keto-thiolases catalyzing the condensation of acetyl-CoA to acetoacetyl-CoA (such as the AtoB or phaA genes) can be attenuated.

In some embodiments using hosts that naturally accumulate polyhydroxyalkanoates, the genes (e.g., endogenous genes) encoding polymer synthase enzymes can be attenuated in the host strain.

In some embodiments requiring the intracellular availability of acetyl-CoA for butadiene synthesis, a host that is deficient (e.g., attenuated level of activity) in one or more enzymes in the acetate synthesis pathway can be used. For example, a host that is deficient in a phosphotransacetylase (encoded by the pta gene) can be used (Shen et al., *Appl. Environ. Microbio.*, 2011, 77(9), 2905-2915).

In some embodiments requiring the intracellular availability of acetyl-CoA for butadiene synthesis, a gene (e.g., an endogenous gene) in an acetate synthesis pathway encoding an acetate kinase, such as ack, can be attenuated.

In some embodiments requiring the intracellular availability of acetyl-CoA for butadiene synthesis, a gene (e.g., an endogenous gene) encoding an enzyme catalyzing the degradation of pyruvate to lactate, such as ldhA, can be attenuated (Shen et al., *Appl. Environ. Microbio.*, 2011, 77(9), 2905-2915).

In some embodiments requiring the intracellular availability of acetyl-CoA for butadiene synthesis, a gene (an endogenous gene) encoding an enzyme catalyzing the degradation of phophoenolpyruvate to succinate, such as frdBC, can be attenuated (see, e.g., Shen et al., 2011, supra).

In some embodiments requiring the intracellular availability of acetyl-CoA for butadiene synthesis, a gene (e.g., an endogenous gene) encoding an enzyme catalyzing the degradation of acetyl-CoA to ethanol, such as adhE, can be attenuated (Shen et al., 2011, supra).

In some embodiments requiring the intracellular availability of L-glutamate for butadiene synthesis, the genes (e.g., endogenous genes) encoding enzymes catalyzing anaplerotic reactions supplementing the citric acid cycle intermediates can be amplified.

In some embodiments, where pathways require excess NADPH co-factor in the synthesis of butadiene, a puridine nucleotide transhydrogenase gene, such as UdhA, can be overexpressed in the host organisms (Brigham et al., *Advanced Biofuels and Bioproducts*, 2012, Chapter 39, 1065-1090).

In some embodiments, where pathways require excess NADPH co-factor in the synthesis of butadiene, a glyceraldehyde-3P-dehydrogenase gene such as GapN can be overexpressed in the host organisms (Brigham et al., 2012, supra).

In some embodiments, where pathways require excess NADPH co-factor in the synthesis of butadiene, a malic enzyme gene, such as maeA or maeB can be overexpressed in the host organisms (Brigham et al., 2012, supra).

In some embodiments, where pathways require excess NADPH co-factor in the synthesis of butadiene, a glucose-6-phosphate dehydrogenase gene such as zwf can be overexpressed in the host organisms (Lim et al., *Journal of Bioscience and Bioengineering*, 2002, 93(6), 543-549).

In some embodiments, where pathways require excess NADPH co-factor in the synthesis of butadiene, a fructose 1,6 diphosphatase gene such as fbp can be overexpressed in the host organisms (Becker et al., *Journal of Biotechnology*, 2007, 132, 99-109).

In some embodiments, the efflux of butadiene across the cell membrane to the extracellular media can be enhanced or amplified by genetically engineering structural modifications to the cell membrane or increasing any associated transporter activity for butadiene.

In some embodiments, genes (e.g., endogenous genes) encoding oxygenases degrading butadiene to toxic intermediates such as 1,2-epoxy-3-butene and 1,2:3,4-diepoxybutane can be attenuated in the host organism (see, e.g., Sweeney et al., *Carcinogenesis*, 1997, 18(4), 611-625).

The invention will be further described in the following examples, which do not limit the scope of the invention described in the claims.

EXAMPLES

Example 1

Enzyme Activity of Linalool Dehydratase Using 3-buten-2-ol as Substrate

The his-tagged linalool dehydratase (EC 4.2.1.127) from *Castellaniella defragrans* was cloned into a pARZ4 vector and transformed into *E. coli* BL21. The resulting strain was cultivated and induced using 1M IPTG (isopropylthio-β-galactoside) in a shake flask culture containing Luria Broth media and kanamycin selection pressure.

The cells from each of the induced shake flask cultures were harvested and pelleted by centrifugation. The cell pellet was resuspended and the cells were lysed. The cell debris was separated from the supernatant via centrifugation and filtered using a 0.2 μm filter. The enzyme was purified from the filtered supernatant using Ni-affinity chromatography and concentrated and buffer exchanged using a Vivaspin 15R Centrifugal Concentrator and Hi-trap Desalting column into 80 mM Tris buffer (pH=9).

Non-native enzyme activity assays were undertaken in a buffer containing 11 mM of 3-buten-2-ol at 25° C. The activity assays were undertaken in 2 mL septum-sealed vials, thereby allowing butadiene accumulation in the headspace. The reaction was initiated by adding 1 mL of purified enzyme to the assay buffer containing the substrate.

The headspace was sampled for butadiene analysis by GC-MS (gas chromatography-mass spectrometry). The retention time for the butadiene standard and the assay samples were within 2%. The ratio of the MS ion peak areas from the butadiene standard and the MS ion peak areas of the samples agree to within 20%. Also, the ion peak areas were above the limit of quantitation for the GC-MS.

These findings show that linalool dehydratase (EC 4.2.1.127) accepts 3-buten-2-ol as a substrate, thereby synthesizing butadiene.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of butadiene synthesis, the method comprising introducing a first vinyl group into a first vinyl group acceptor compound of a 1,3-butadiene synthetic pathway using a dehydratase enzyme capable of introducing a first vinyl group into the first vinyl group acceptor compound, wherein the dehydratase enzyme capable of introducing the first vinyl group is linalool dehydratase (EC 4.2.1.127), 5-hydroxyvaleryl-CoA dehydratase from *C. viride*, or a dehydratase from species *Aquincola tertiaricarbonis* or *Methylibium petroleiphilum* PM1.

2. The method of claim 1, wherein the method comprises a fermentation process using a host cell expressing the dehydratase enzyme that catalyzes the introduction of a first vinyl group in a first vinyl group acceptor compound of a 1,3-butadiene synthetic pathway.

3. The method according to claim 2, wherein the host cell is either a prokaryote or a eukaryote.

4. The method according to claim 3, wherein the prokaryote is of the genus *Escherichia* such as *Escherichia coli*; of the genus *Clostridia* such as *Clostridium ljungdahlii*, *Clostridium autoethanogenum* or *Clostridium kluyveri*; of the genus *Corynebacteria* such as *Corynebacterium glutamicum*; of the genus *Cupriavidus* such as *Cupriavidus necator* or *Cupriavidus metallidurans*; of the genus *Pseudomonas* such as *Pseudomonas fluorescens* or *Pseudomonas putida*; of the genus *Bacillus* such as *Bacillus subtillis*; or of the genus *Rhodococcus* such as *Rhodococcus equi*.

5. The method according to claim 3, wherein the eukaryote is of the genus *Aspergillus* such as *Aspergillus niger*; of the genus *Saccharomyces* such as *Saccharomyces cerevi-*

*siae*; of the genus *Pichia* such as *Pichia pastoris*; of the genus *Yarrowia* such as *Yarrowia lipolytica; of the genus Issatchenkia* such as *Issathenkia orientalis*; of the genus *Debaryomyces* such as *Debaryomyces hansenii*; of the genus *Arxula* such as *Arxula adenoinivorans*; or of the genus *Kluyveromyces* such as *Kluyveromyces lactis*.

6. The method according to claim 2, wherein the fermentation process comprises anaerobic, micro-aerobic or aerobic cell cultivation.

7. The method according to claim 2, wherein cell retention strategies using ceramic hollow fibre membranes are employed to achieve and maintain a high cell density during fermentation.

8. The method according to claim 2, wherein the principal carbon source fed to the fermentation derives from biological or non-biological feedstocks.

9. The method according to claim 8, where the biological feedstock is, or derives from, monosaccharides, disaccharides, hemicellulose such as levulinic acid and furfural, cellulose, lignocellulose, lignin, triglycerides such as glycerol and fatty acids, agricultural waste or municipal waste.

10. The method according to claim 8, where the non-biological feedstock is, or derives from, natural gas, syngas, $CO_2/H_2$, methanol, ethanol, non-volatile residue (NVR), caustic wash from a cyclohexane oxidation processes, or other waste stream from the chemical or petrochemical industries.

11. The method of claim 2, wherein the host cell further comprises a decarboxylating thioesterase enzyme that introduces a second vinyl group into a second vinyl group acceptor compound of a 1,3-butadiene synthetic pathway.

12. A method for the biosynthesis of butadiene comprising introducing a first vinyl group into a first vinyl group acceptor compound of a 1,3-butadiene synthetic pathway using a linalool dehydratase (EC 4.2.1.127), 5-hydroxyvaleryl-CoA dehydratase from *C. viride*, or a dehydratase from species *Aquincola tertiaricarbonis* or *Methylibium petroleiphilum* PM1, or a functional fragment or variant thereof having at least 25% of an activity and containing not more than 50 amino acid additions, deletions, or substitutions relative to a corresponding wild-type sequence of linalool dehydratase (EC 4.2.1.127), 5-hydroxyvaleryl-CoA dehydratase from *C. viride*, or a dehydratase from species *Aquincola tertiaricarbonis* or *Methylibium petroleiphilum* PM1.

\* \* \* \* \*